US007118593B2

(12) United States Patent
Davidson et al.

(10) Patent No.: US 7,118,593 B2
(45) Date of Patent: *Oct. 10, 2006

(54) EXTENDIBLE STENT APPARATUS

(75) Inventors: Charles J. Davidson, Winnetka, IL (US); Eric Williams, Pleasanton, CA (US); Gil M. Vardi, Town and Country, MI (US); Stuart Lin, Sunnyvale, CA (US)

(73) Assignee: Advanced Stent Technologies, Inc., Concord, CA (US)

( * ) Notice: Subject to any disclaimer, the term of this patent is extended or adjusted under 35 U.S.C. 154(b) by 450 days.

This patent is subject to a terminal disclaimer.

(21) Appl. No.: 10/683,165

(22) Filed: Oct. 14, 2003

(65) Prior Publication Data

US 2004/0133268 A1    Jul. 8, 2004

Related U.S. Application Data

(63) Continuation of application No. 09/963,114, filed on Sep. 24, 2001, now Pat. No. 6,706,062, which is a continuation of application No. 09/326,445, filed on Jun. 4, 1999, now Pat. No. 6,325,826, and a continuation-in-part of application No. PCT/US99/00835, filed on Jan. 13, 1999.

(60) Provisional application No. 60/088,301, filed on Jun. 5, 1998.

(51) Int. Cl.
*A61F 2/06* (2006.01)
(52) U.S. Cl. ..................... 623/1.15; 623/1.35
(58) Field of Classification Search ............... 623/1.35, 623/1.18, 1.15, 1.13, 1.12, 1.3; 606/190, 606/194, 195, 198, 200
See application file for complete search history.

(56) References Cited

U.S. PATENT DOCUMENTS

| 1,596,754 A | 8/1926 | Moschelle |
| 3,657,744 A | 4/1972 | Ersek |
| 3,872,893 A | 3/1975 | Roberts |

(Continued)

FOREIGN PATENT DOCUMENTS

CA        2318314        7/1999

(Continued)

OTHER PUBLICATIONS

Serruys et al., *The New England Journal of Medicine*, vol. 331, No. 8, pp. 489-495 (1994).

(Continued)

*Primary Examiner*—Cary E. O'Connor
(74) *Attorney, Agent, or Firm*—Vidas, Arrett, Steinkraus

(57) ABSTRACT

The present invention concerns novel stent apparatuses for use in treating lesions at or near the bifurcation point in bifurcated cardiac, coronary, renal, peripheral vascular, gastrointestinal, pulmonary, urinary and neurovascular vessels and brain vessels. More particularly, the invention concerns a stent apparatus with at least one side opening which may further comprise an extendable stent portion laterally extending from the side opening and at least partly in registry with the wall of the side opening. Devices constructed in accordance with the invention include, singularly or in combination, a main expandable stent comprising at least one substantially circular side opening located between its proximal and distal end openings, which side opening may further comprise an expandable portion extending radially outward from the edges of the side opening; and a branch stent comprising proximal and distal end openings and which may further comprise a contacting portion at its proximal end, and which may optionally be constructed to form either a perpendicular branch or a non-perpendicular branch when inserted through a side opening of the main stent. The stents of the invention are marked with, or at least partially constructed of, a material which is imageable during intraluminal catheterization techniques, most preferably but not limited to ultrasound and x-ray.

14 Claims, 18 Drawing Sheets

U.S. PATENT DOCUMENTS

| | | |
|---|---|---|
| 4,140,126 A | 2/1979 | Choudhury |
| 4,309,994 A | 1/1982 | Grunwald |
| 4,410,476 A | 10/1983 | Redding et al. |
| 4,413,989 A | 11/1983 | Schjeldahl |
| 4,421,810 A | 12/1983 | Rasmussen |
| 4,453,545 A | 6/1984 | Inoue |
| 4,503,569 A | 3/1985 | Dotter |
| 4,552,554 A | 11/1985 | Gould et al. |
| 4,681,570 A | 7/1987 | Dalton |
| 4,689,174 A | 8/1987 | Lupke |
| 4,731,055 A | 3/1988 | Melinyshyn et al. |
| 4,733,665 A | 3/1988 | Palmaz |
| 4,739,762 A | 4/1988 | Palmaz |
| 4,759,748 A | 7/1988 | Reed |
| 4,762,128 A | 8/1988 | Rosenbluth |
| 4,769,029 A | 9/1988 | Patel |
| 4,819,664 A | 4/1989 | Nazari |
| 4,872,874 A | 10/1989 | Taheri |
| 4,878,495 A | 11/1989 | Grayzel |
| 4,896,670 A | 1/1990 | Crittenden |
| 4,900,314 A | 2/1990 | Quackenbush |
| 4,906,244 A | 3/1990 | Pinchuk et al. |
| 4,909,258 A | 3/1990 | Kuntz et al. |
| 4,957,501 A | 9/1990 | Lahille et al. |
| 4,957,508 A | 9/1990 | Kaneko et al. |
| 4,964,850 A | 10/1990 | Bouton et al. |
| 4,983,167 A | 1/1991 | Sahota |
| 4,994,071 A | 2/1991 | MacGregor |
| 5,042,976 A | 8/1991 | Ishitsu et al. |
| 5,054,501 A | 10/1991 | Chuttani et al. |
| 5,059,177 A | 10/1991 | Towne et al. |
| 5,061,240 A | 10/1991 | Cherian |
| 5,064,435 A | 11/1991 | Porter |
| 5,102,403 A | 4/1992 | Alt |
| 5,102,417 A | 4/1992 | Palmaz |
| 5,104,404 A | 4/1992 | Wolff |
| 5,117,831 A | 6/1992 | Jang |
| 5,122,125 A | 6/1992 | Deuss |
| 5,135,536 A | 8/1992 | Hillstead |
| 5,147,317 A | 9/1992 | Shank et al. |
| 5,159,920 A | 11/1992 | Condon et al. |
| 5,176,617 A | 1/1993 | Fischell et al. |
| 5,192,297 A | 3/1993 | Hull |
| 5,217,440 A | 6/1993 | Frassica |
| 5,244,619 A | 9/1993 | Burnham |
| 5,257,974 A | 11/1993 | Cox |
| 5,263,932 A | 11/1993 | Jang |
| 5,282,472 A | 2/1994 | Companion et al. |
| 5,304,220 A | 4/1994 | Maginot |
| 5,320,605 A | 6/1994 | Sahota |
| 5,324,257 A | 6/1994 | Osborne et al. |
| 5,337,733 A | 8/1994 | Bauerfeind et al. |
| 5,338,300 A | 8/1994 | Cox |
| 5,342,295 A | 8/1994 | Imran |
| 5,342,297 A | 8/1994 | Jang |
| 5,350,395 A | 9/1994 | Yock |
| 5,383,892 A | 1/1995 | Ansel |
| 5,387,235 A | 2/1995 | Chuter |
| 5,395,332 A | 3/1995 | Ressemann et al. |
| 5,395,334 A | 3/1995 | Keith et al. |
| 5,404,887 A | 4/1995 | Prather |
| 5,409,458 A | 4/1995 | Khairkhahan et al. |
| 5,413,581 A | 5/1995 | Goy |
| 5,413,586 A | 5/1995 | Dibie et al. |
| 5,417,208 A | 5/1995 | Winkler |
| 5,437,638 A | 8/1995 | Bowman |
| 5,443,497 A | 8/1995 | Venbrux |
| 5,445,624 A | 8/1995 | Jimenez |
| 5,449,373 A | 9/1995 | Pinchasik et al. |
| 5,449,382 A | 9/1995 | Dayton |
| 5,456,694 A | 10/1995 | Marin et al. |
| 5,456,712 A | 10/1995 | Maginot |
| 5,456,714 A | 10/1995 | Owen |
| 5,458,605 A | 10/1995 | Klemm |
| 5,462,530 A | 10/1995 | Jang |
| 5,489,271 A | 2/1996 | Anderson |
| 5,489,295 A | 2/1996 | Piplani et al. |
| 5,496,292 A | 3/1996 | Burnham |
| 5,505,702 A | 4/1996 | Arney |
| 5,507,768 A | 4/1996 | Lau et al. |
| 5,507,769 A | 4/1996 | Marin et al. |
| 5,514,154 A | 5/1996 | Lau et al. |
| 5,522,801 A | 6/1996 | Wang |
| 5,531,788 A | 7/1996 | Dibie et al. |
| 5,545,132 A | 8/1996 | Fagan et al. |
| 5,549,553 A | 8/1996 | Ressemann et al. |
| 5,549,554 A | 8/1996 | Miraki |
| 5,562,620 A | 10/1996 | Klein et al. |
| 5,562,724 A | 10/1996 | Vorwerk et al. |
| 5,562,725 A | 10/1996 | Schmitt et al. |
| 5,569,295 A | 10/1996 | Lam |
| 5,571,087 A | 11/1996 | Ressemann et al. |
| 5,575,771 A | 11/1996 | Walinsky |
| 5,575,818 A | 11/1996 | Pinchuk |
| 5,591,228 A | 1/1997 | Edoga |
| 5,593,442 A | 1/1997 | Klein |
| 5,607,444 A | 3/1997 | Lam |
| 5,609,625 A | 3/1997 | Piplani et al. |
| 5,609,627 A | 3/1997 | Goicoechea et al. |
| 5,609,629 A | 3/1997 | Fearnot et al. |
| 5,613,949 A | 3/1997 | Miraki |
| 5,613,980 A | 3/1997 | Chauhan |
| 5,613,981 A | 3/1997 | Boyle et al. |
| 5,617,878 A | 4/1997 | Taheri |
| 5,626,600 A | 5/1997 | Horzewski et al. |
| 5,628,788 A | 5/1997 | Pinchuk |
| 5,632,762 A | 5/1997 | Myler |
| 5,632,763 A | 5/1997 | Glastra |
| 5,632,772 A | 5/1997 | Alcime et al. |
| 5,634,902 A | 6/1997 | Johnson et al. |
| 5,639,278 A | 6/1997 | Dereume et al. |
| 5,643,340 A | 7/1997 | Nunokawa |
| 5,653,743 A | 8/1997 | Martin |
| 5,662,614 A | 9/1997 | Edoga |
| 5,669,924 A | 9/1997 | Shaknovich |
| 5,669,932 A | 9/1997 | Fischell et al. |
| 5,676,696 A | 10/1997 | Morcade |
| 5,676,697 A | 10/1997 | McDonald |
| 5,679,400 A | 10/1997 | Tuch |
| 5,690,642 A | 11/1997 | Osborne et al. |
| 5,693,084 A | 12/1997 | Chutter |
| 5,693,086 A | 12/1997 | Goicoechea et al. |
| 5,697,971 A | 12/1997 | Fischell et al. |
| 5,707,354 A | 1/1998 | Salmon et al. |
| 5,709,713 A | 1/1998 | Evans et al. |
| 5,716,365 A | 2/1998 | Goicoechea et al. |
| 5,718,683 A | 2/1998 | Ressemann et al. |
| 5,718,724 A | 2/1998 | Goicoechea et al. |
| 5,720,735 A | 2/1998 | Dorros |
| 5,723,004 A | 3/1998 | Dereume et al. |
| 5,724,977 A | 3/1998 | Yock et al. |
| 5,728,158 A | 3/1998 | Lau et al. |
| 5,733,303 A | 3/1998 | Israel et al. |
| 5,735,893 A | 4/1998 | Lau et al. |
| 5,746,766 A | 5/1998 | Edoga |
| 5,749,825 A | 5/1998 | Fischell et al. |
| 5,749,848 A | 5/1998 | Jang et al. |
| 5,755,734 A | 5/1998 | Richter et al. |
| 5,755,735 A | 5/1998 | Richter et al. |
| 5,755,770 A | 5/1998 | Ravenscroft |
| 5,755,771 A | 5/1998 | Penn et al. |
| 5,755,778 A | 5/1998 | Kleshinski |
| 5,762,631 A | 6/1998 | Klein |
| 5,776,101 A | 7/1998 | Goy |

| | | | | | | |
|---|---|---|---|---|---|---|
| 5,776,161 | A | 7/1998 | Globerman | 6,183,509 B1 | 2/2001 | Dibie |
| 5,776,180 | A | 7/1998 | Goicoechea et al. | 6,190,403 B1 | 2/2001 | Fischell et al. |
| 5,800,450 | A | 9/1998 | Lary et al. | 6,203,569 B1 | 3/2001 | Wijay |
| 5,800,508 | A | 9/1998 | Goicoechea et al. | 6,210,380 B1 | 4/2001 | Mauch |
| 5,814,061 | A | 9/1998 | Osborne et al. | 6,210,429 B1 | 4/2001 | Vardi |
| 5,817,126 | A | 10/1998 | Imran | 6,217,527 B1 | 4/2001 | Selmon et al. |
| 5,824,008 | A | 10/1998 | Bolduc et al. | 6,217,608 B1 | 4/2001 | Penn et al. |
| 5,824,036 | A | 10/1998 | Lauterjung | 6,221,080 B1 | 4/2001 | Power |
| 5,824,040 | A | 10/1998 | Cox et al. | 6,221,090 B1 | 4/2001 | Wilson |
| 5,824,044 | A | 10/1998 | Quiachon et al. | 6,221,098 B1 | 4/2001 | Wilson et al. |
| 5,827,320 | A | 10/1998 | Richter et al. | 6,231,563 B1 | 5/2001 | White et al. |
| 5,833,650 | A | 11/1998 | Imran | 6,231,598 B1 | 5/2001 | Berry et al. |
| 5,836,966 | A | 11/1998 | St. Germain | 6,231,600 B1 | 5/2001 | Zhong |
| 5,837,008 | A | 11/1998 | Berg et al. | 6,235,051 B1 | 5/2001 | Murphy |
| 5,843,031 | A | 12/1998 | Hermann et al. | 6,241,762 B1 | 6/2001 | Shanley |
| 5,843,160 | A | 12/1998 | Rhodes | 6,258,073 B1 | 7/2001 | Mauch |
| 5,843,164 | A | 12/1998 | Frantzen et al. | 6,258,099 B1 | 7/2001 | Mareiro et al. |
| 5,846,204 | A | 12/1998 | Solomon | 6,258,116 B1 | 7/2001 | Hojeibane |
| 5,851,210 | A | 12/1998 | Torossian | 6,258,121 B1 | 7/2001 | Yang et al. |
| 5,851,464 | A | 12/1998 | Davila et al. | 6,261,273 B1 | 7/2001 | Ruiz |
| 5,855,600 | A | 1/1999 | Alt | 6,261,305 B1 | 7/2001 | Marotta et al. |
| 5,855,601 | A | 1/1999 | Bessler et al. | 6,261,319 B1 | 7/2001 | Kveen et al. |
| 5,865,178 | A | 2/1999 | Yock | 6,264,682 B1 | 7/2001 | Wilson et al. |
| 5,868,777 | A | 2/1999 | Lam | 6,273,911 B1 | 8/2001 | Cox et al. |
| 5,871,537 | A | 2/1999 | Holman et al. | 6,273,913 B1 | 8/2001 | Wright et al. |
| 5,891,133 | A | 4/1999 | Murphy-Chutorian | 6,287,314 B1 | 9/2001 | Lee et al. |
| 5,897,588 | A | 4/1999 | Hull et al. | 6,290,673 B1 | 9/2001 | Shanley |
| 5,906,640 | A | 5/1999 | Penn et al. | 6,293,967 B1 | 9/2001 | Shanley |
| 5,907,893 | A | 6/1999 | Zadno-Azizi et al. | 6,299,634 B1 | 10/2001 | Bergeron |
| 5,913,895 | A | 6/1999 | Burpee et al. | 6,302,906 B1 | 10/2001 | Goicoechea et al. |
| 5,913,897 | A | 6/1999 | Corso, Jr. et al. | 6,309,412 B1 | 10/2001 | Lau et al. |
| 5,921,958 | A | 7/1999 | Ressemann et al. | 6,309,414 B1 | 10/2001 | Rolando et al. |
| 5,922,020 | A | 7/1999 | Klein et al. | 6,312,459 B1 | 11/2001 | Huang et al. |
| 5,928,248 | A | 7/1999 | Acker | 6,325,821 B1 | 12/2001 | Gaschino et al. |
| 5,938,682 | A | 8/1999 | Hojeibane | 6,325,826 B1 | 12/2001 | Vardi et al. |
| 5,938,696 | A | 8/1999 | Goicoechea et al. | 6,334,870 B1 | 1/2002 | Her et al. |
| 5,948,016 | A | 9/1999 | Jang | 6,346,089 B1 | 2/2002 | Dibie |
| 5,951,599 | A | 9/1999 | McCrory | 6,361,544 B1 | 3/2002 | Wilson et al. |
| 5,961,548 | A | 10/1999 | Shmulewitz | 6,361,555 B1 | 3/2002 | Wilson |
| 5,967,986 | A | 10/1999 | Cimochowski et al. | 6,383,215 B1 | 5/2002 | Sass |
| 5,972,018 | A | 10/1999 | Israel et al. | 6,387,120 B1 | 5/2002 | Wilson et al. |
| 6,007,517 | A | 12/1999 | Anderson | 6,395,018 B1 | 5/2002 | Castaneda |
| 6,013,054 | A | 1/2000 | Juin Yan | 6,398,792 B1 | 6/2002 | O'Connor |
| 6,013,091 | A | 1/2000 | Ley et al. | 6,398,804 B1 | 6/2002 | Spielberg |
| 6,017,363 | A | 1/2000 | Hojeibane | 6,428,570 B1 | 8/2002 | Globerman |
| 6,030,414 | A | 2/2000 | Taheri | 6,432,133 B1 | 8/2002 | Lau et al. |
| 6,033,434 | A | 3/2000 | Borghi | 6,436,104 B1 | 8/2002 | Hojeibane |
| 6,033,435 | A | 3/2000 | Penn et al. | 6,436,134 B1 | 8/2002 | Richter et al. |
| 6,036,682 | A | 3/2000 | Lange et al. | 6,478,816 B1 | 11/2002 | Kveen et al. |
| 6,039,749 | A | 3/2000 | Marin et al. | 6,482,211 B1 | 11/2002 | Choi |
| 6,042,597 | A | 3/2000 | Kveen et al. | 6,485,511 B1 | 11/2002 | Lau et al. |
| 6,045,557 | A | 4/2000 | White et al. | 6,494,905 B1 | 12/2002 | Zedler et al. |
| 6,048,361 | A | 4/2000 | Von Oepen | 6,511,504 B1 | 1/2003 | Lau et al. |
| 6,056,775 | A | 5/2000 | Borghi et al. | 6,511,505 B1 | 1/2003 | Cox et al. |
| 6,059,823 | A | 5/2000 | Holman et al. | 6,520,988 B1 | 2/2003 | Colombo et al. |
| 6,059,824 | A | 5/2000 | Taheri | 6,527,799 B1 | 3/2003 | Shanley |
| 6,066,168 | A | 5/2000 | Lau et al. | 6,540,719 B1 | 4/2003 | Bigus et al. |
| 6,068,655 | A | 5/2000 | Seguin et al. | 6,540,779 B1 | 4/2003 | Richter et al. |
| 6,071,285 | A | 6/2000 | Lashinski et al. | 6,572,647 B1 | 6/2003 | Supper |
| 6,086,611 | A | 7/2000 | Duffy et al. | 6,579,309 B1 | 6/2003 | Loos et al. |
| 6,090,127 | A | 7/2000 | Globerman | 6,579,312 B1 | 6/2003 | Wilson et al. |
| 6,090,128 | A | 7/2000 | Douglas | 6,582,394 B1 | 6/2003 | Reiss et al. |
| 6,096,073 | A | 8/2000 | Webster et al. | 6,582,459 B1 | 6/2003 | Lau et al. |
| 6,099,497 | A | 8/2000 | Adams et al. | 6,596,022 B1 | 7/2003 | Lau et al. |
| 6,117,117 | A | 9/2000 | Mauch | 6,599,316 B1 | 7/2003 | Vardi et al. |
| 6,117,156 | A | 9/2000 | Richter et al. | 2001/0012927 A1 | 8/2001 | Mauch |
| 6,129,738 | A | 10/2000 | Lashinski et al. | 2001/0016767 A1 | 8/2001 | Wilson et al. |
| 6,129,754 | A | 10/2000 | Kanesaka et al. | 2001/0016768 A1 | 8/2001 | Wilson et al. |
| 6,142,973 | A | 11/2000 | Carleton et al. | 2001/0027291 A1 | 10/2001 | Shanley |
| 6,152,945 | A | 11/2000 | Bachinski et al. | 2001/0027338 A1 | 10/2001 | Greenberg |
| 6,165,195 | A | 12/2000 | Wilson et al. | 2001/0029396 A1 | 10/2001 | Wilson et al. |
| 6,165,197 | A | 12/2000 | Yock | 2001/0037116 A1 | 11/2001 | Wilson et al. |
| 6,179,867 | B1 | 1/2001 | Cox | 2001/0037138 A1 | 11/2001 | Wilson et al. |

| | | | | | | |
|---|---|---|---|---|---|---|
| 2001/0037146 | A1 | 11/2001 | Lau et al. | WO | WO 92/19308 | 11/1992 |
| 2001/0037147 | A1 | 11/2001 | Lau et al. | WO | WO 95/21592 | 8/1995 |
| 2001/0039395 | A1 | 11/2001 | Mareiro et al. | WO | WO 96/41592 | 12/1996 |
| 2001/0039448 | A1 | 11/2001 | Dibie | WO | WO 97/09946 | 3/1997 |
| 2001/0047201 | A1 | 11/2001 | Cox et al. | WO | WO 97/16217 | 5/1997 |
| 2001/0049552 | A1 | 12/2001 | Richter et al. | WO | WO 97/26936 | 7/1997 |
| 2001/0056297 | A1 | 12/2001 | Hojeibane | WO | WO 97/33532 | 9/1997 |
| 2002/0013618 | A1 | 1/2002 | Marotta et al. | WO | WO 97/41803 | 11/1997 |
| 2002/0013619 | A1 | 1/2002 | Shanley | WO | WO 97/45073 | 12/1997 |
| 2002/0022874 | A1 | 2/2002 | Wilson | WO | WO 98/17204 | 4/1998 |
| 2002/0026232 | A1 | 2/2002 | Marotta et al. | WO | WO 98/19628 | 5/1998 |
| 2002/0032478 | A1 | 3/2002 | Bockstegers et al. | WO | WO 98/35634 | 8/1998 |
| 2002/0035392 | A1 | 3/2002 | Wilson | WO | WO 98/36709 | 8/1998 |
| 2002/0042650 | A1 | 4/2002 | Vardi et al. | WO | WO 98/37833 | 9/1998 |
| 2002/0052648 | A1 | 5/2002 | McGuckin et al. | WO | WO 98/44871 | 10/1998 |
| 2002/0058990 | A1 | 5/2002 | Jang | WO | WO 98/48733 | 11/1998 |
| 2002/0072790 | A1 | 6/2002 | McGuckin et al. | WO | WO 98/52497 | 11/1998 |
| 2002/0107564 | A1 | 8/2002 | Cox et al. | WO | WO 99/15103 | 4/1999 |
| 2002/0111675 | A1 | 8/2002 | Wilson | WO | WO 99/17680 | 4/1999 |
| 2002/0123790 | A1 | 9/2002 | White et al. | WO | WO 99/34749 | 7/1999 |
| 2002/0123797 | A1 | 9/2002 | Majercak | WO | WO 99/36002 | 7/1999 |
| 2002/0123798 | A1 | 9/2002 | Burgermeister | WO | WO 99/39661 | 8/1999 |
| 2002/0151959 | A1 | 10/2002 | Von Oepen | WO | WO 99/58059 | 11/1999 |
| 2002/0156516 | A1 | 10/2002 | Vardi et al. | WO | WO 99/65419 | 12/1999 |
| 2002/0156517 | A1 | 10/2002 | Perouse | WO | WO 00/00104 | 1/2000 |
| 2002/0165604 | A1 | 11/2002 | Shanley | WO | WO 00/12166 | 3/2000 |
| 2002/0173835 | A1 | 11/2002 | Bourang et al. | WO | WO 00/13613 | 3/2000 |
| 2002/0173840 | A1 | 11/2002 | Brucker et al. | WO | WO 00/53122 | 9/2000 |
| 2002/0177892 | A1 | 11/2002 | Globerman | WO | WO 00/74595 | 12/2000 |
| 2002/0183763 | A1 | 12/2002 | Callol et al. | WO | WO 01/21095 | 3/2001 |
| 2002/0193872 | A1 | 12/2002 | Trout et al. | WO | WO 01/21109 | 3/2001 |
| 2002/0193873 | A1 | 12/2002 | Brucker et al. | WO | WO 01/21244 | 3/2001 |
| 2003/0004535 | A1 | 1/2003 | Musbach et al. | WO | WO 01/70299 | 9/2001 |
| 2003/0009209 | A1 | 1/2003 | Hojeibane | WO | WO 02/68012 | 9/2002 |
| 2003/0009214 | A1 | 1/2003 | Shanley | WO | WO 02/76333 | 10/2002 |
| 2003/0014102 | A1 | 1/2003 | Hong et al. | WO | WO 02/94336 | 11/2002 |
| 2003/0023301 | A1 | 1/2003 | Cox et al. | WO | WO 03/55414 | 7/2003 |
| 2003/0050688 | A1 | 3/2003 | Fischell et al. | | | |
| 2003/0074047 | A1 | 4/2003 | Richter | | | |

OTHER PUBLICATIONS

Fischmann et al., *The New England Journal of Medicine*, vol. 331, No. 8, pp. 496-501 (1994).

Nakamura et al., *Catheterization & Cardiovascular Diagnosis* 34-353-361 (1995).

Caputo et al., *The American Journal of Cardiology*, vol. 7, pp. 1226-1230 (1996).

Colombo et al., *Catheterization and Cardiovascular Diagnosis*, vol. 30, pp. 327-330 (1993).

Carrie et al., *Catheterization and Cardiovascular Diagnosis*, vol. 37, pp. 311-313 (1996).

Katoh et al., *Catheterization and Cardiovascular Diagnosis*, vol. 40, pp. 400-402 (1997).

SCIMED Life Systems, Inc. - TRIO™ 14 PTCA Catheter, Re-engineering Over-the-Wire Balloon Technology, Company Brochure, © 1994.

Lewis et al., *American Heart Journal*, vol. 127, pp. 1600-1607 (1994).

Dichek, D.A. et al.; *Circulation*, 80; 1347-1353 (1989).

Chevalier, B. et al.; *American Journal of Cardiology*, 82: 943-949 (1998).

Yamashita, T. et al.; *Journal of American College of Cardiology*, 35: 1145-1151 (2000).

Satler, S., et al.; *Catheterization & Cardiovascular Interventions*, 50: 411-412 (2000).

| | | | |
|---|---|---|---|
| 2003/0093109 | A1 | 5/2003 | Mauch |
| 2003/0114912 | A1 | 6/2003 | Sequin et al. |
| 2003/0114915 | A1 | 6/2003 | Mareiro et al. |
| 2003/0125791 | A1 | 7/2003 | Sequin et al. |
| 2003/0125799 | A1 | 7/2003 | Limon et al. |
| 2003/0125802 | A1 | 7/2003 | Callol et al. |
| 2004/0015227 | A1 | 1/2004 | Vardi et al. |

FOREIGN PATENT DOCUMENTS

| | | |
|---|---|---|
| DE | 29701758 | 5/1997 |
| EP | 684022 | 11/1995 |
| EP | 804907 | 5/1997 |
| EP | 876805 | 11/1998 |
| EP | 884028 | 12/1998 |
| EP | 891751 | 1/1999 |
| EP | 897698 | 2/1999 |
| EP | 897700 | 2/1999 |
| EP | 904745 | 3/1999 |
| EP | 1031328 | 8/2000 |
| EP | 1031330 | 8/2000 |
| FR | 2678508 | 1/1993 |
| WO | WO 88/06026 | 8/1988 |
| WO | WO 90/13332 | 11/1990 |
| WO | WO 91/12779 | 9/1991 |

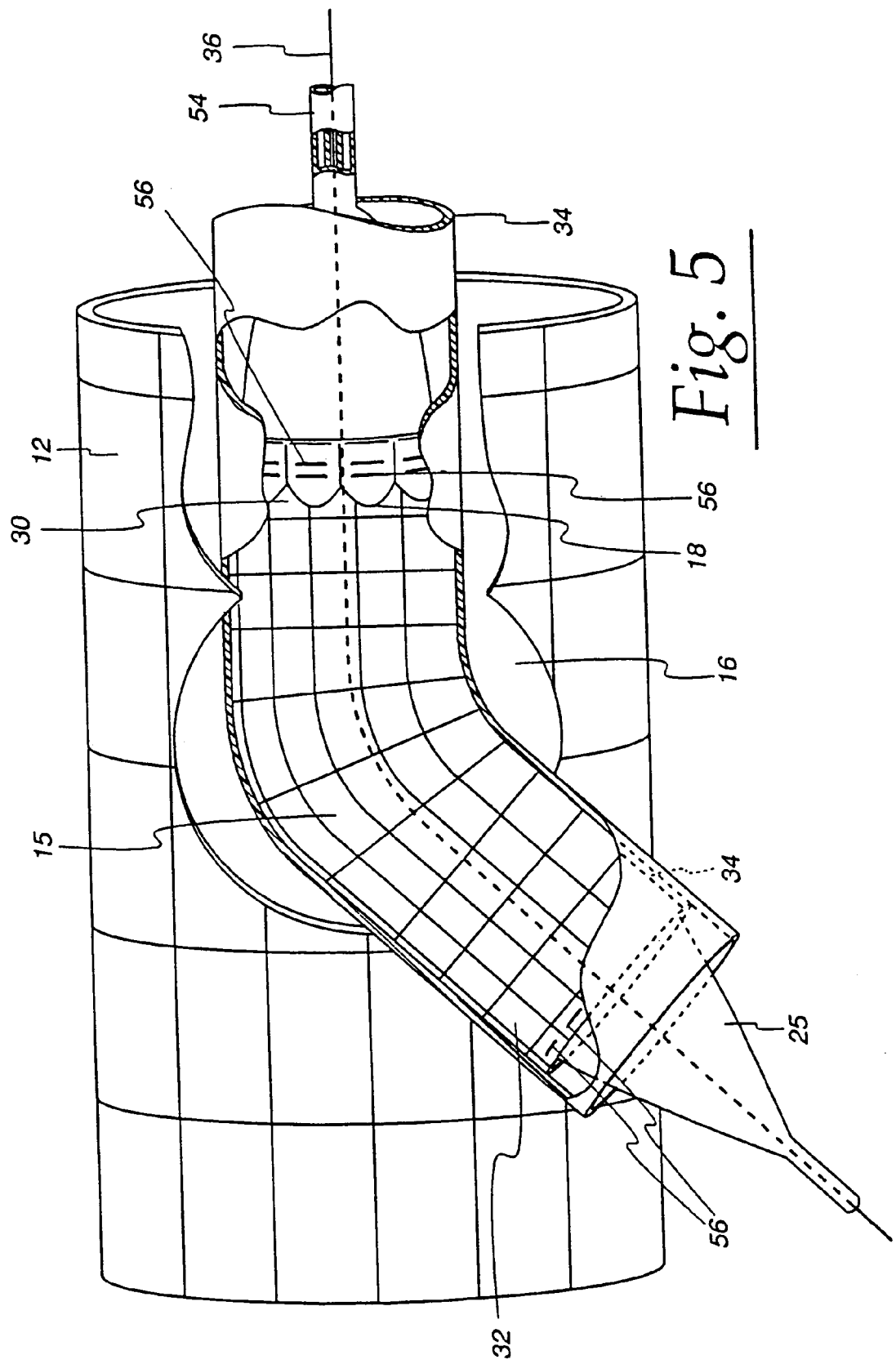

*Fig. 13a*
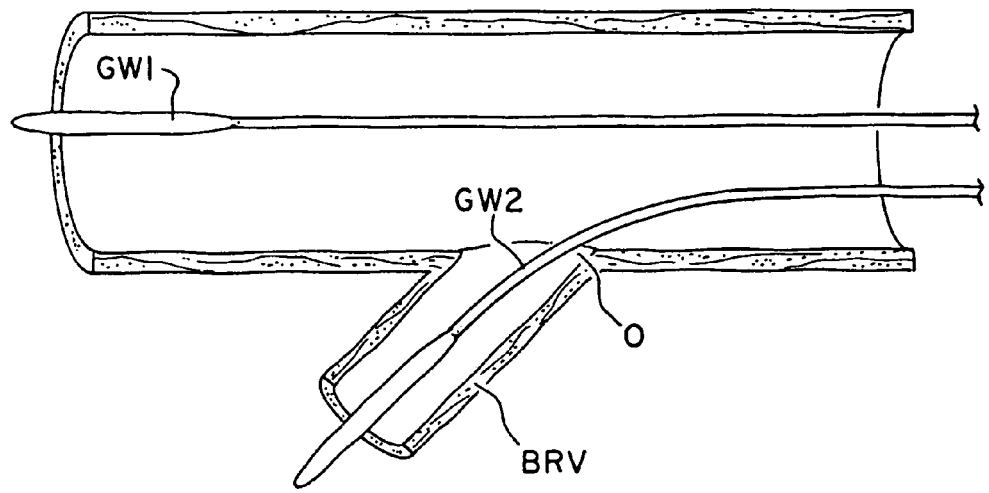
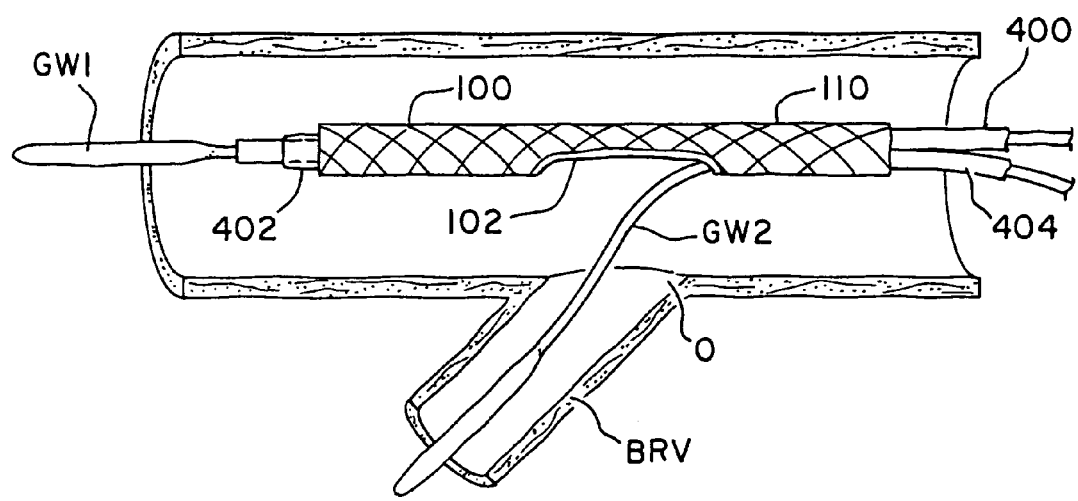
*Fig. 13b*

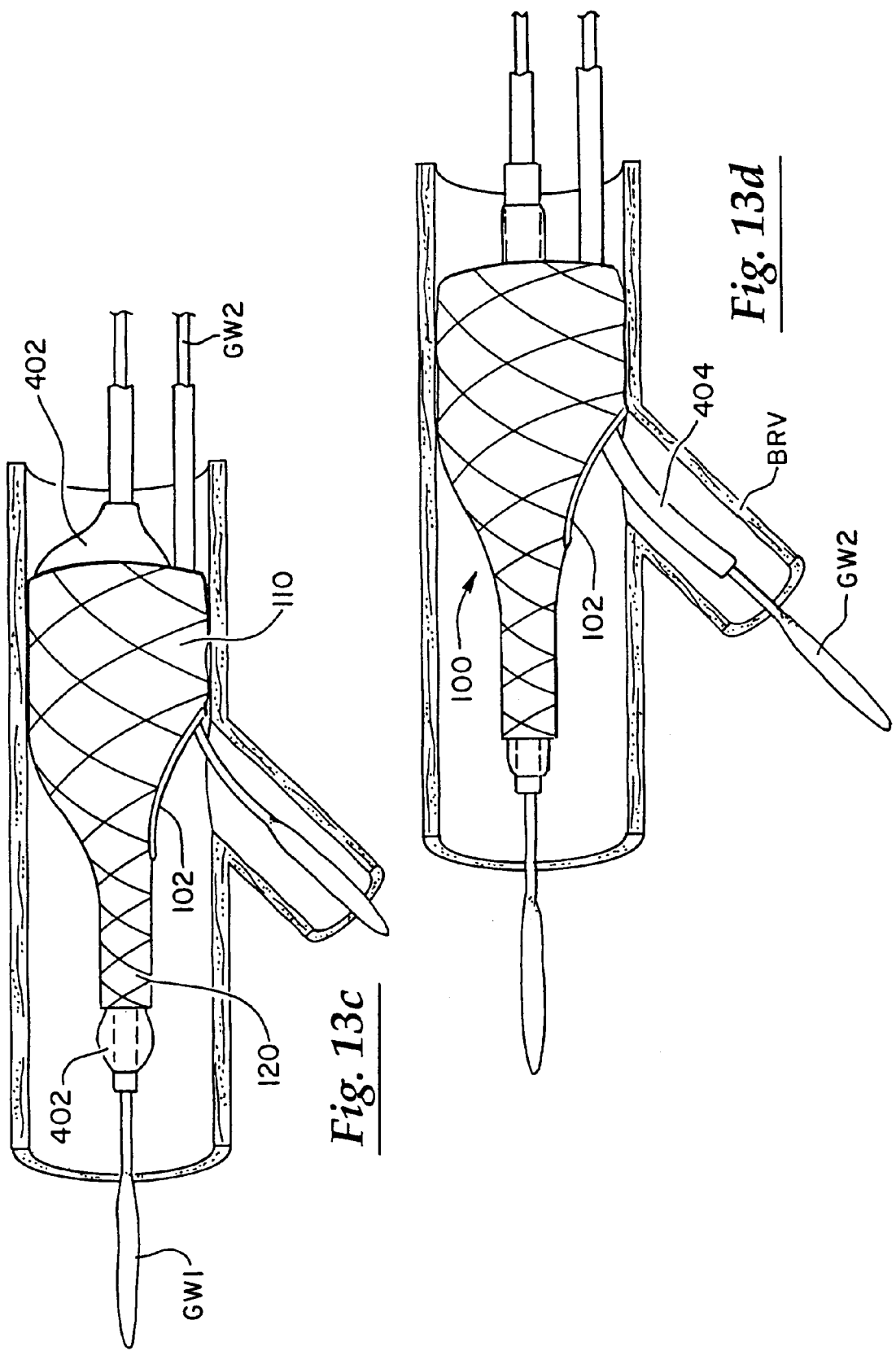

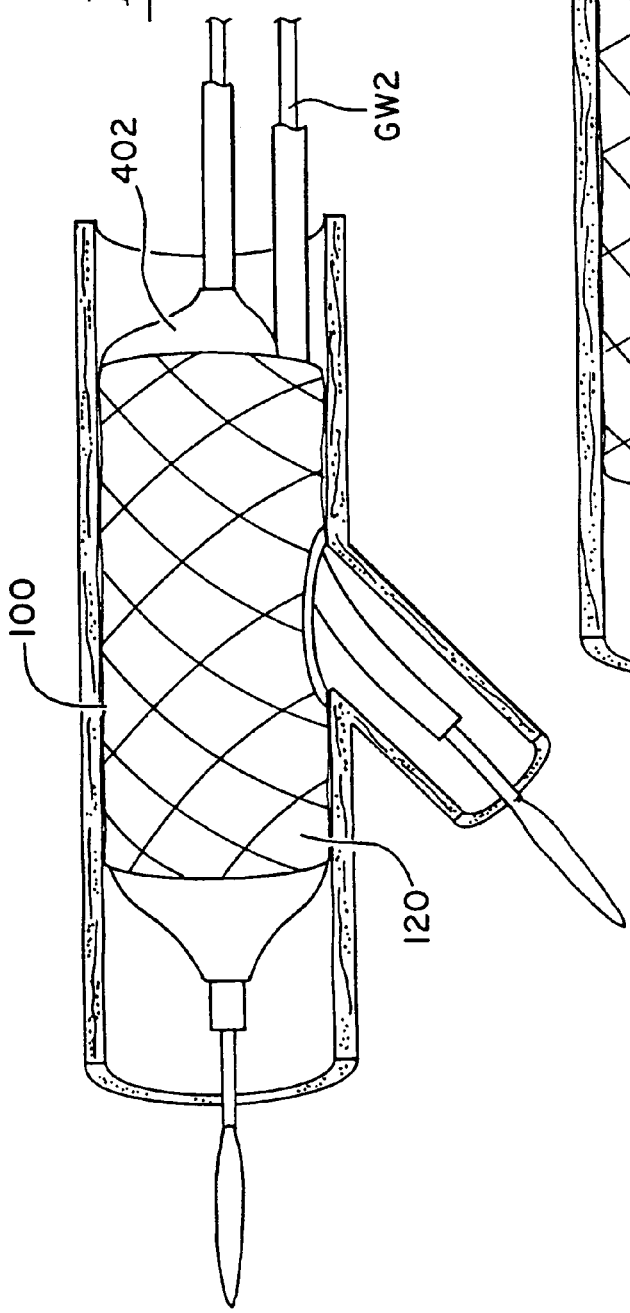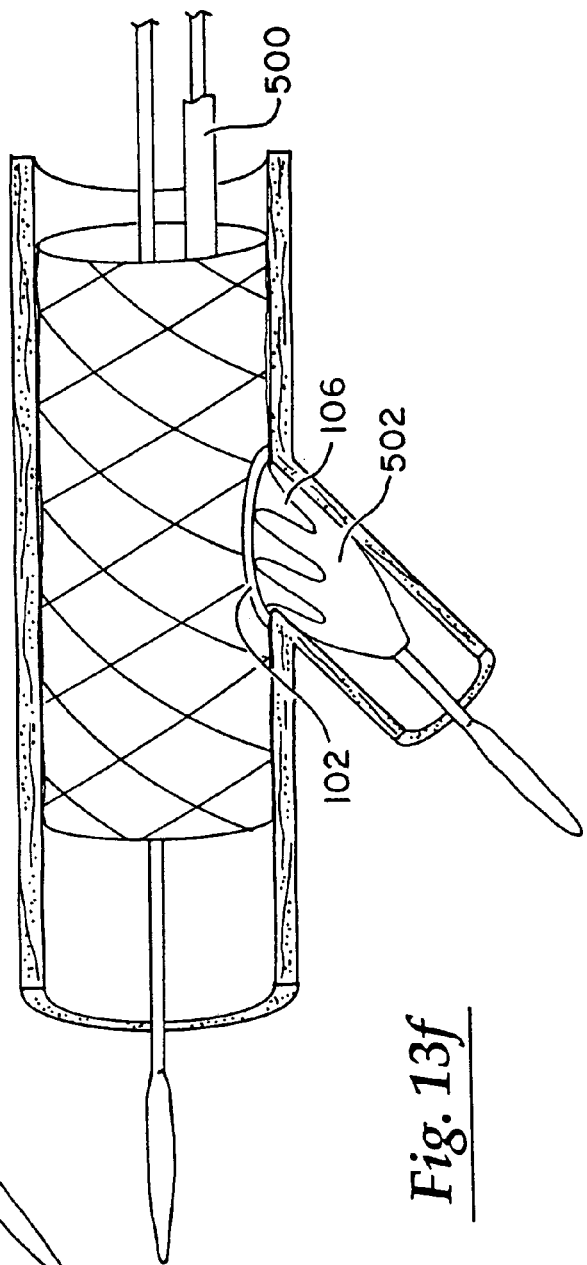

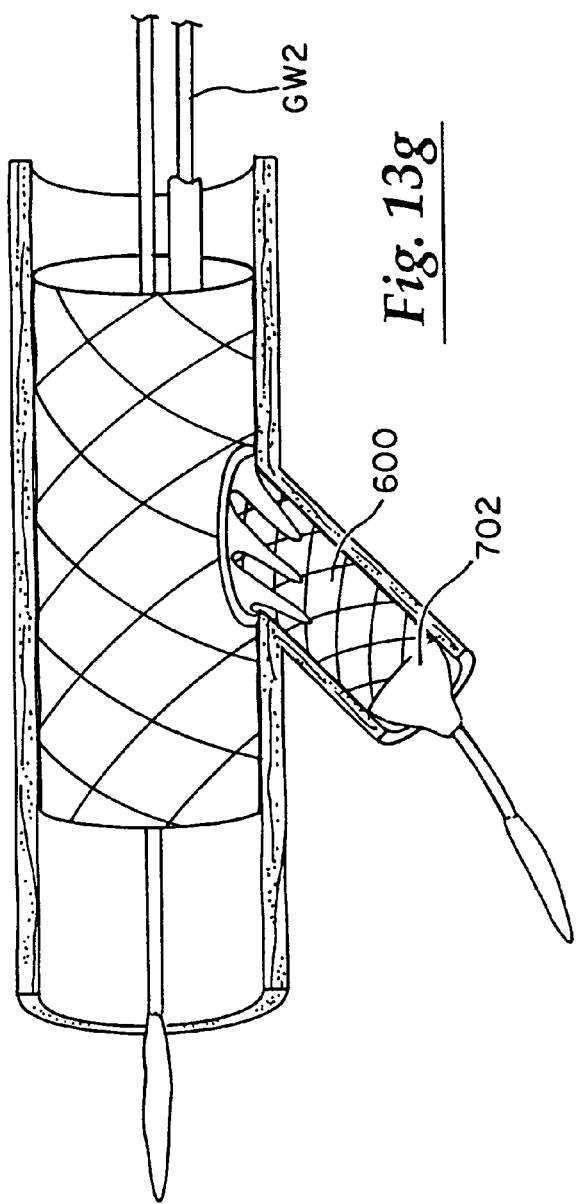
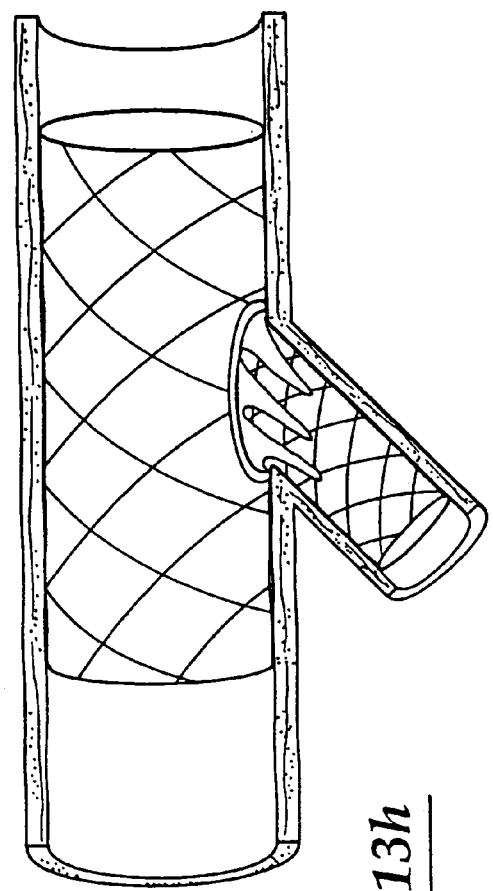

EXTENDIBLE STENT APPARATUS

CROSS-REFERENCES TO RELATED APPLICATIONS

This application is a continuation of application Ser. No. 09/963,114, filed Sep. 24, 2001, now U.S. Pat. No. 6,706,062, which is a continuation of application Ser. No. 09/326,445, filed on Jun. 4, 1999, now U.S. Pat. No. 6,325,826, which claims priority to Provisional Application No. 60/088,301, filed Jun. 5, 1998; and is a continuation-in-part of PCT Patent Application PCT/US99/00835, Jan. 13, 1999, published as WO 99/36002, the disclosures of which are incorporated herein in their entirety for all purposes.

BACKGROUND OF THE INVENTION

A type of endoprosthesis device, commonly referred to as a stent, may be placed or implanted within a vein, artery or other tubular body organ for treating occlusions, stenoses, or aneurysms of a vessel by reinforcing the wall of the vessel or by expanding the vessel. Stents have been used to treat dissections in blood vessel walls caused by balloon angioplasty of the coronary arteries as well as peripheral arteries and to improve angioplasty results by preventing elastic recoil and remodeling of the vessel wall. Two randomized multicenter trials have recently shown a lower restenosis rate in stent treated coronary arteries compared with balloon angioplasty alone (Serruys, P W et al. New England Journal of Medicine 331: 489–495, 1994, Fischman, D L et al. New England Journal of Medicine 331: 496–501, 1994). Stents have been successfully implanted in the urinary tract, the bile duct, the esophagus and the tracheo-bronchial tree to reinforce those body organs, as well as implanted into the neurovascular, peripheral vascular, coronary, cardiac, and renal systems, among others. The term "stent" as used in this Application is a device which is intraluminally implanted within bodily vessels to reinforce collapsing, dissected, partially occluded, weakened, diseased or abnormally dilated or small segments of a vessel wall.

One of the drawbacks of conventional stents is that they are generally produced in a straight tubular configuration. The use of such stents to treat diseased vessels at or near a bifurcation (branch point) of a vessel may create a risk of compromising the degree of patency of the primary vessel and/or its branches, or the bifurcation point and also limits the ability to insert a second stent into the side branch if the result of treatment of the primary, or main, vessel is suboptimal. Suboptimal results may occur as a result of several mechanisms, such as displacing diseased tissue, plaque shifting, vessel spasm, dissection with or without intimal flaps, thrombosis, and embolism.

The risk of branch compromise is increased generally in two anatomical situations. First, a side branch may be compromised when there is a stenosis in the origin of the side branch. Second, when there is an eccentric lesion at the bifurcation site, asymmetric expansion can cause either plaque shifting or dissection at the side branch origin. There are reports of attempts to solve this problem by inserting a balloon into the side branch through the struts of a stent deployed in the main branch spanning the bifurcation point; however, this technique carries the risk of balloon entrapment and other major complications (Nakamura, S. et al., Catheterization and Cardiovascular Diagnosis 34: 353–361 (1995)). Moreover, adequate dilation of the side branch is limited by elastic recoil of the origin of the side branch. In addition, insertion of a traditional stent into a main vessel spanning a the bifurcation point may pose a limitation to blood flow and access to the side branch vessel. The term "stent jail" is often used to describe this concept. In this regard, the tubular slotted hinged design of the Palmaz-Schatz intracoronary stent, in particular, is felt to be unfavorable for lesions with a large side branch and is generally believed to pose a higher risk of side branch vessel entrapment where the stent prevents or limits access to the side branch. Id.

One common procedure for intraluminally implanting a stent is to first open the relevant region of the vessel with a balloon catheter and then place the stent in a position that bridges the treated portion of the vessel in order to prevent elastic recoil and restenosis of that segment. The angioplasty of the bifurcation lesion has traditionally been performed using the "kissing" balloon technique where two guidewires and two balloons are inserted, one into the main branch and the other into the side branch. Stent placement in this situation requires the removal of the guidewire from the side branch and reinsertion through the stent struts, followed by the insertion of a balloon through the struts of the stent along the guidewire. The first removal of the guidewire poses the risk of occlusion of the side branch during the deployment of the stent in the main branch.

In general, when treating a bifurcation lesion using commercially available stents, it is important to cover the origin of the branch because if left uncovered, this area is prone to restenosis. In order to cover the branch origin, conventional stents inserted into the branch must protrude into the lumen of the main artery or vessel from the branch (which may cause thrombosis, again compromising blood flow). Another frequent complication experienced when stenting bifurcated vessels is the narrowing or occlusion of the origin of a side branch spanned by a stent placed in the main branch. Additionally, placement of a stent into a main vessel where the stent partially or completely extends across the opening of a branch makes future access into such branch vessels difficult if not impossible. As a result, conventional stents are often placed into the branch close to the origin, but generally not covering the origin of the bifurcation.

Lastly, conventional stents are difficult to visualize during and after deployment, and in general are not readily imaged by using low-cost and easy methods such as x-ray or ultrasound imaging. While some prior art balloon catheters (and not stents) are "marked" at the proximal and distal ends of the balloon with imageable patches, few stents are currently available which are marked with or which are at least partly constructed of, a material which is imageable by currently known imaging procedures commonly used when inserting the stents into a vessel, such as ultrasound or x-ray imaging. The invention described in this Application would not work with endoscopy as currently used as an imaging method due to size limitations, but future advances in limiting the size of endoscopic imaging devices may in the future make endoscopic imaging compatible with the stents of the invention.

Accordingly, there is a need for improved stent apparatuses, most particularly for applications within the cardiac, coronary, renal, peripheral vascular, gastrointestinal, pulmonary, urinary and neurovascular systems and the brain which 1) completely covers the bifurcation point of bifurcation vessels; 2) may be used to treat lesions in one branch of a bifurcation while preserving access to the other branch for future treatment; 3) allows for differential sizing of the stents in a bifurcated stent apparatus even after the main stent is implanted; 4) may be delivered intraluminally by catheter; 5) may be used to treat bifurcation lesions in a bifurcated vessel where the branch vessel extends from the side of the main vessel; and 6) is marked with, or at least partly constructed of, material which is imageable by commonly used intraluminal catheterization visualization techniques including but not limited to ultrasound or x-ray.

SUMMARY OF THE INVENTION

The present invention concerns novel stent apparatuses for methods, and kits use in treating lesions at or near the bifurcation point in bifurcated vessels. More particularly, the invention concerns a stent apparatus with a main tubular stent body having at least one side opening which may further comprise an extendable or second stent inserted through the side opening and at least partly in registry with the wall of the side opening.

As used herein, the term "vessel" means any body lumen or tubular tissue within the cardiac, coronary, renal, peripheral vascular, gastrointestinal, pulmonary, urinary and neurovascular systems and the brain. Devices constructed in accordance with the invention include, singularly or in combination, a main expandable tubular stent body having at least one side opening (usually substantially circular) located between its proximal and distal end openings, which side opening may further comprise a radially expandable portion extending laterally outward from the edges of the side opening; and an expandable branch second stent comprising proximal and distal end openings and which may further comprise a contacting portion at its proximal end, and which may be constructed to form an angularly variable branched stent apparatus when inserted through a side opening of the main stent. The radially expandable portion preferably comprises a plurality of laterally deployable elements, such as loops, tabs, beams, or the like, attached or coupled to a peripheral edge of the side opening. Usually, the elements will project inwardly from the periphery into the side hole so that they may be deployed radially outwardly from the periphery to open in a petal-like fashion. The elements may be formed integrally as part of the tubular body structure, e.g., being formed from the bent wire or band or from the cut tubular structure which defines the stent structure. Alternatively, they could be formed separately and subsequently attached by crimping, welding, folding, interference fitting, etc. Optionally, the expandable portion may be covered with a fabric or the entire stent structure membrane to help form the transition between the main body lumen and the lumen of the second stent. The stents of the invention are marked with, or at least partially constructed of, a material which is imageable during intraluminal catheterization techniques, most preferably but not limited to ultrasound and x-ray, preferably being radiopaque.

In a preferred aspect of the stent design, the side hole will be defined by a continuous band or pattern of material which defines the periphery of the side hole. The band may have a circular, oval, or other regular geometry in which case the width and area of the side hole will remain generally constant as the stent is expanded. Alternatively, the continuous band may comprise discontinuities over its length so that the area and/or width of the side hole may expand together with the stent structure. Preferably, the continuous band will include inwardly projecting loops, fingers, or other protrusions which will define the laterally deployable elements which project inwardly from the peripheral edge of the side opening. The inwardly projecting loops or other elements may be overlapping or non-overlapping. The use of overlapping looped structures maximizes the length of the inwardly projecting elements after they are unfolded and opened inwardly into the side branch, as described in more detail below.

In another aspect of the present invention, a stent for placement in a bifurcated body lumen comprises a main tubular body having a first end, a second end, and a side opening therebetween. A first portion of the main tubular body between the first end and the side hole opens in response to a first radially outward pressure, typically provided by an expansion balloon. A second portion of the main tubular body between the side hole and the second end opens in response to a second pressure, again typically applied by an expansion balloon. By constructing the main tubular body so that the first opening pressure is less than the second opening pressure, the stent can have differential opening characteristics. That is, by introducing a balloon expansion catheter into the stent and applying a constant pressure over the entire length of the balloon, the first portion of the stent will yield and open before the second portion of the stent. The particular embodiments described below, the first yield pressure will typically be in the range from 1 atmospheres to 10 atmospheres while the second yield pressure will typically be in the range from 2 atmospheres to 18 atmospheres. Such stent structures may be placed by initially opening and deploying the first portion, typically the proximal portion on the same side of the bifurcation as the deployment catheter, and thereafter positioning the side hole to align more precisely with the bifurcated secondary blood vessel. After the proper positioning has been achieved, the second stent portion can then be opened, conveniently using the same expansion balloon which has been inflated to a higher inflation pressure. Such stents will typically include the laterally deployable elements disposed around the side opening, as described above, and will optionally be used in combination with secondary stents, as described above.

The stent structures as described previously may combine conventional stent elements, such as serpentine rings, diamond or box structures, axial expansion members, and the like. In addition, in order to provide the differential expansion characteristics, the main tubular bodies of the stents may include axial spine structures which differ from the remaining portions of the tubular body of the stent. For example, the first portion of the stent may have an axial spine which readily expands circumferentially. By then providing a spine section on the second portion of the stent which is more resistant to circumferential expansion, the desired differential expansion will be achieved. Alternatively, the differential expansion can be achieved by employing stent patterns which are uniformly easier or more difficult to radially expand over their entire peripheral length. Specific examples of both structures will be described below.

The stent apparatuses of the invention offers significant and novel advantages over prior art stents in that the stents of the invention 1) can completely cover the bifurcation point of a branched vessel; 2) can accommodate main and branch stents of differing sizes, thus providing a better fit where the main and branch vessels are of different sizes or where the main and branch vessels are occluded to different degrees; 3) can fit branched vessels where the branch extends laterally from the side of the main vessel; 4) may be used to treat lesions in one branch of a bifurcation while preserving complete access to the other branch for future treatment; 5) may be delivered intraluminally by catheter; and 6) are marked with, or at least partly constructed of, material which is imageable by commonly used intraluminal catheterization visualization techniques including but not limited to ultrasound or x-ray, but not endoscopy.

Thus, it is an object of the present invention to provide both a double-stent apparatus and a single-stent apparatus, each of which may be used to cover the origin of a bifurcation in a branched vessel.

Another object of the invention is to provide a single-stent apparatus which may be used to treat only one branch of a bifurcation lesion while leaving access to the second branch unobstructed.

Additionally, it is an object of the invention to provide a stent apparatus which is itself imageable by methods commonly used during catheterization such as x-ray or ultrasound.

Yet another object of the invention is to provide a bifurcating double-stent device wherein the main stent and the branch stent or stents may be of different sizes.

Lastly, it is an important object of the invention to provide a stent apparatus which may be used to treat bifurcated vessels where the vessel bifurcation extends laterally from the side of the main vessel.

These objects and other object advantages and features of the invention will become better understood from the detailed description of the invention and the accompanying drawings.

BRIEF DESCRIPTION OF THE DRAWINGS

FIG. 5 is a schematic depiction of the double-stent bifurcating stent apparatus, where the main stent is deployed and showing the placement of the branch stent apparatus prior to full deployment of the branch stent.

FIGS. 13A–13H illustrate the deployment of any one of the stents of FIGS. 10–12 in a bifurcated blood vessel or a secondary stent is placed through the side hole of the main stent.

Figure 1:
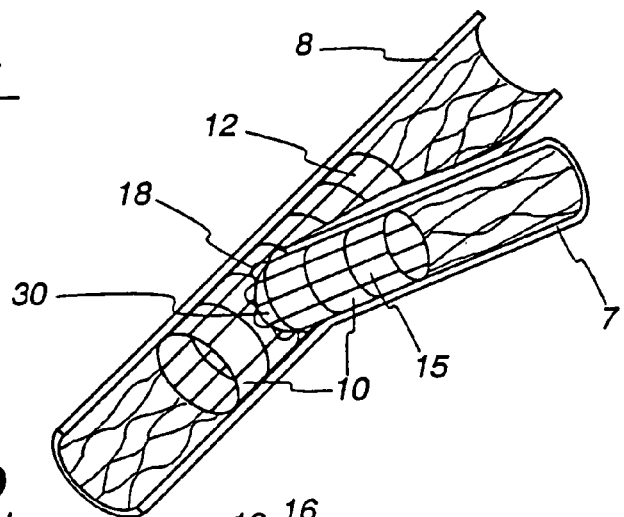
FIG. 1 is a schematic depiction of the double-stent apparatus of the present invention in which both the main stent and the branch stent are fully dilated.

The rectilinear matrices shown in the drawings are intended to show the shapes of the surfaces only, and do not illustrate the actual surface patterns or appearances of the stent apparatuses of the invention.

DESCRIPTION OF THE SPECIFIC EMBODIMENTS

The bifurcating double-stent apparatus 10 of the present invention comprises a generally cylindrical main stent 12 and a generally cylindrical branch stent 15, which are shown as fully dilated in a subject main vessel 8 and a subject branch vessel 7, as illustrated in FIG. 1.

Figure 2:
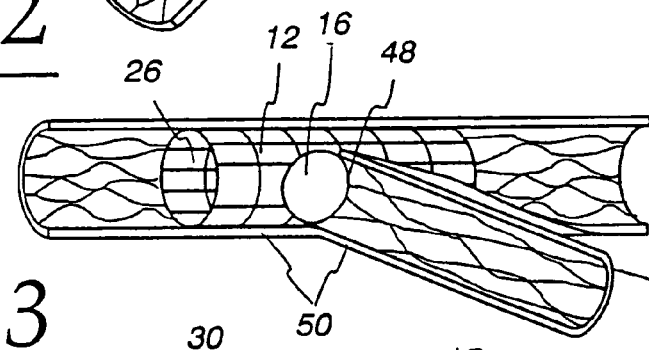
FIG. 2 is a schematic depiction of the main stent of the apparatus of the invention as deployed, with the side opening in registry with a vessel bifurcation point.

The main stent 12 contains at least one generally circular side opening 16 located between the proximal end 26 and the distal end 28 of the main stent 12 (FIG. 2), which opening is positioned over and in registry with the opening 48 of a branch vessel in a vessel bifurcation 50, as shown in FIG. 2. The stent 12 and the side opening are imaged during imaging procedures either by constructing the stent of imageable materials or by placing markers 56 at appropriate locations, such as around the perimeter of the side opening 16 in the main stent 12, and at the proximal end 26 and distal end 28 of the main stent, as illustrated in FIG. 4.

Figure 4:
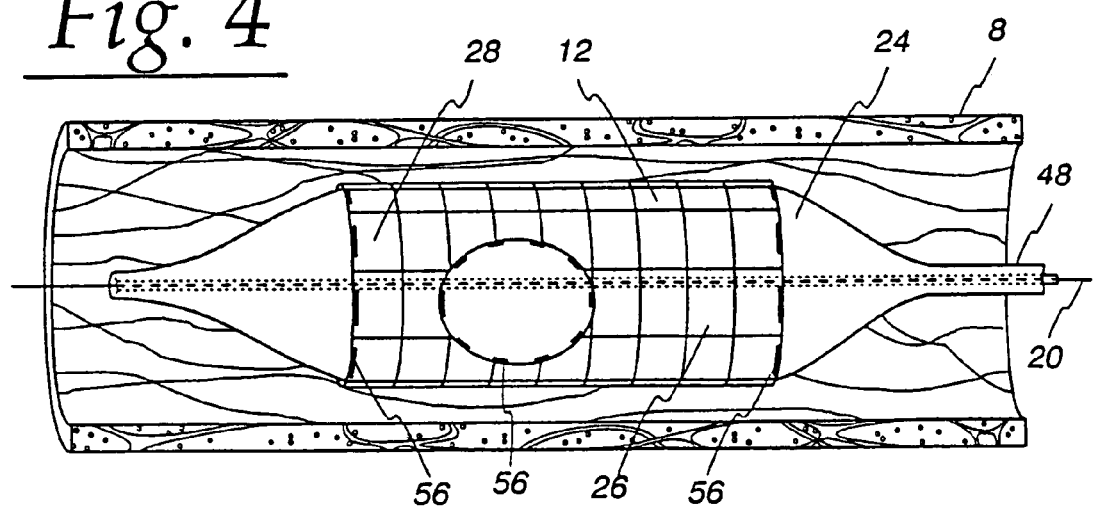
FIG. 4 is a schematic depiction of the main stent of the apparatus deployed within a subject vessel, after inflation of a balloon to expand the main stent to fit the walls of the subject vessel.

As shown in the embodiment of the invention illustrated in FIG. 4, a guidewire 20 is inserted into the vessel 8 prior to insertion of the main stent 12, and is used to guide the main stent 12 into position within the vessel 8. Prior to insertion and expansion, the main stent 12 is disposed around the distal end of a catheter 48 which may include an inflatable balloon 24. The main stent/catheter apparatus is then threaded onto the main guidewire 20 and into the vessel 8. The main stent 12 is radially expanded by inflation of the balloon 24 until it expands the walls of the vessel 8, and is thus affixed into place.

Figure 3:
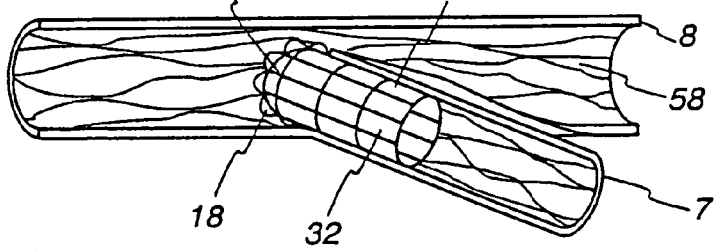
FIG. 3 is a schematic depiction of the branch stent of the apparatus as deployed, with the contacting portion fully expanded to contact the origin of the bifurcated vessel.

In a second embodiment of the invention, the branch stent apparatus 15 of the present invention comprises a generally cylindrical stent comprising a proximal end 30 and a distal end 32, as shown in FIG. 3. The proximal end 30 comprises a contacting portion illustrated here as extended loops 18, which contacting portion, when expanded, is positioned within the lumen 58 of the main vessel 8 (FIG. 3) and at least partially contacting the perimeter of the side opening 16 of the main stent 12. FIG. 4 illustrates the positioning of the main stent 12 (without optional contacting portion) in the main vessel 8 as fully expanded by inflation of the balloon 24.

Figure 7:
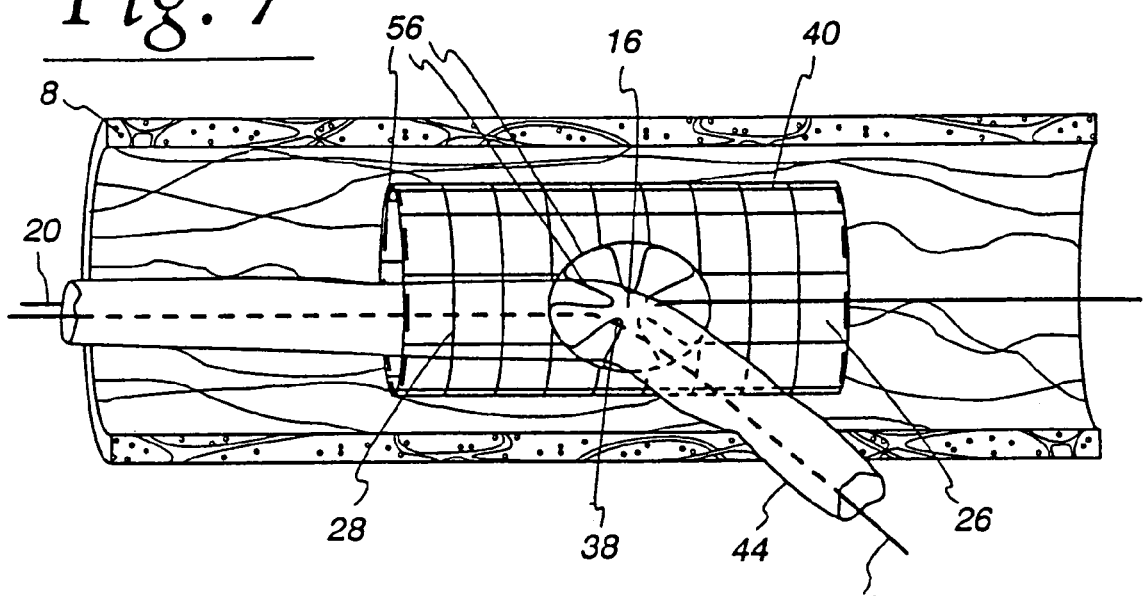
FIG. 7 is a schematic depiction of the main stent with optional expandable portion, prior to balloon expansion of the expandable portion.

As shown in the embodiments illustrated in FIGS. 4, 5 and 7, the ends of the main stent 12 and the expandable branch stent 15 and the contacting portion 18 are visible during insertion by placing imageable markers 56 around the ends of the main 12 and branch 15 stents and the contacting portion 18 and at the proximal end 30 and distal end 32 of the branch stent. Alternatively, the stent may be at least partially constructed of material which is imageable by methods including but not limited to ultrasound or x-ray imaging (but not endoscopic imaging).

Figure 6A:
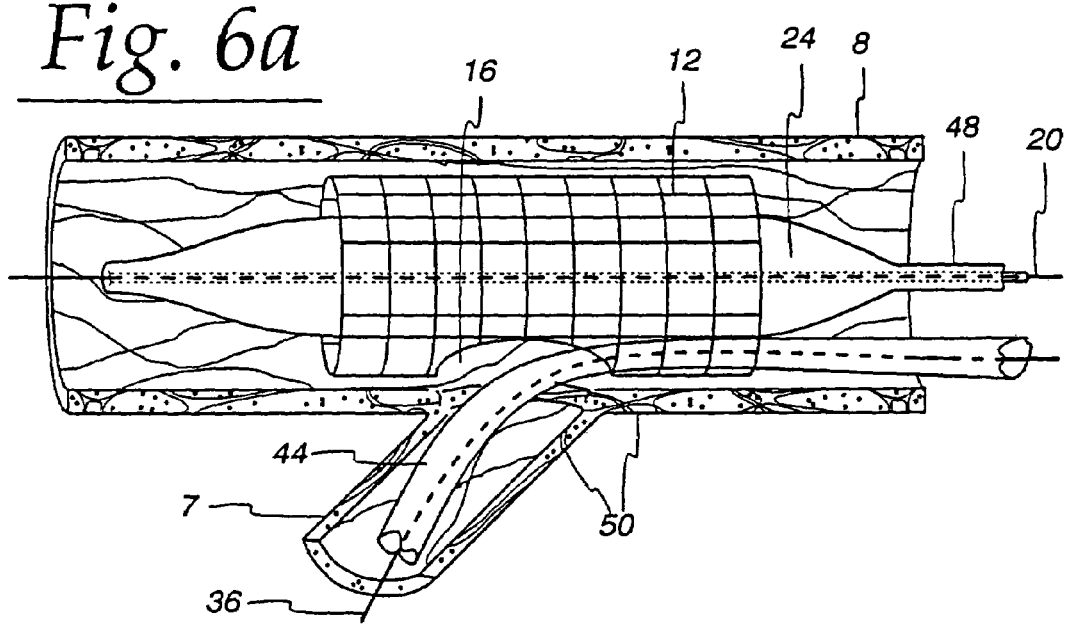
FIG. 6a depicts initial placement of the main stent of the bifurcating stent apparatus into the vessel, along with the insertion of a guidewire and stabilizing catheter for placement of the branch stent into the branch vessel of the subject.
Figure 6B:
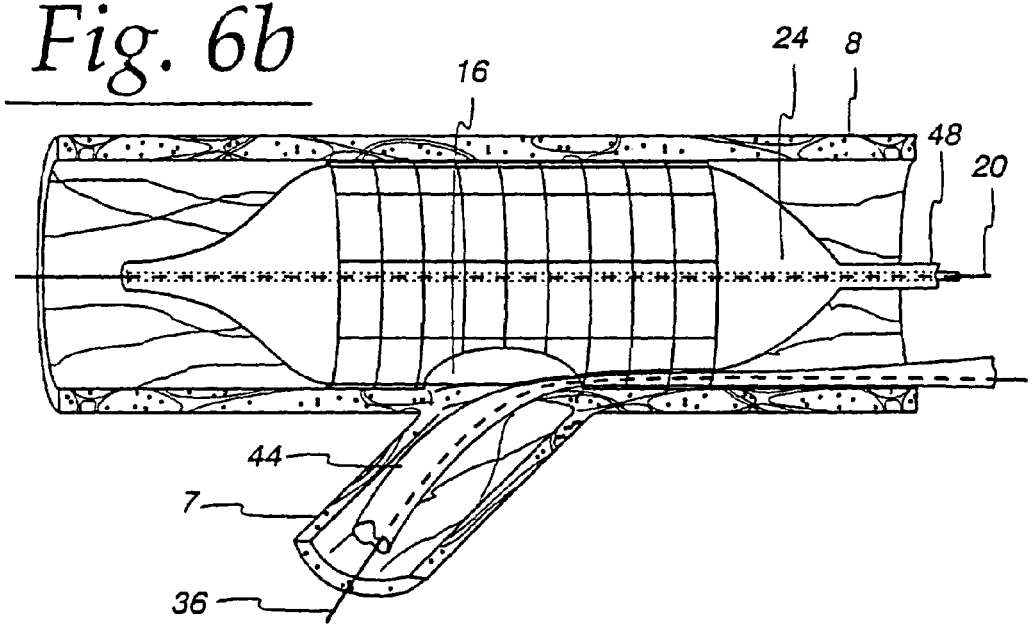
FIG. 6b is a schematic depiction showing the main stent of the invention expanded by balloon expansion.
Figure 6C:
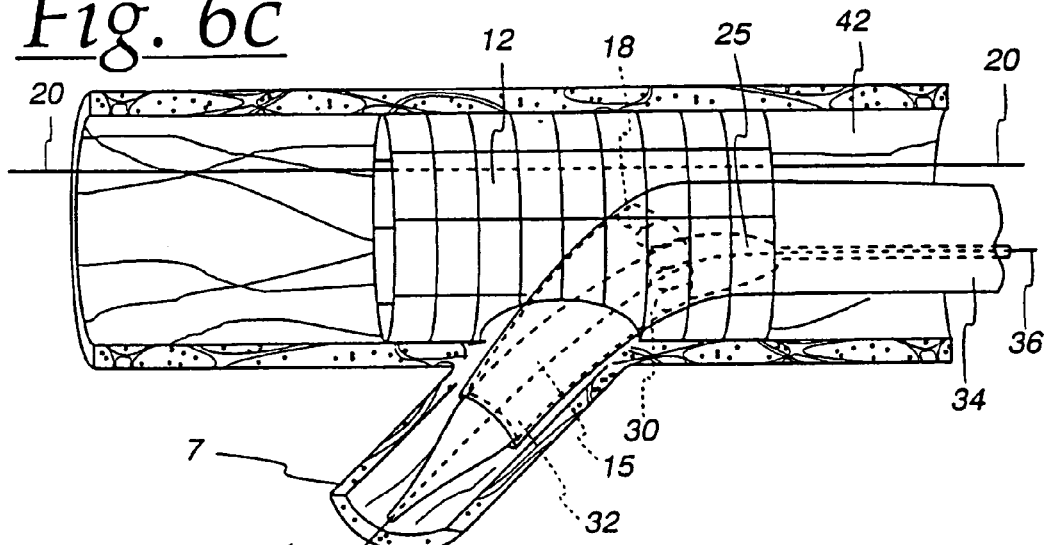
FIG. 6c is a schematic depiction of the deployment of the branch stent over the side branch guidewire, through one of the side openings in the main stent and into the branch vessel of the subject.
Figure 6D:
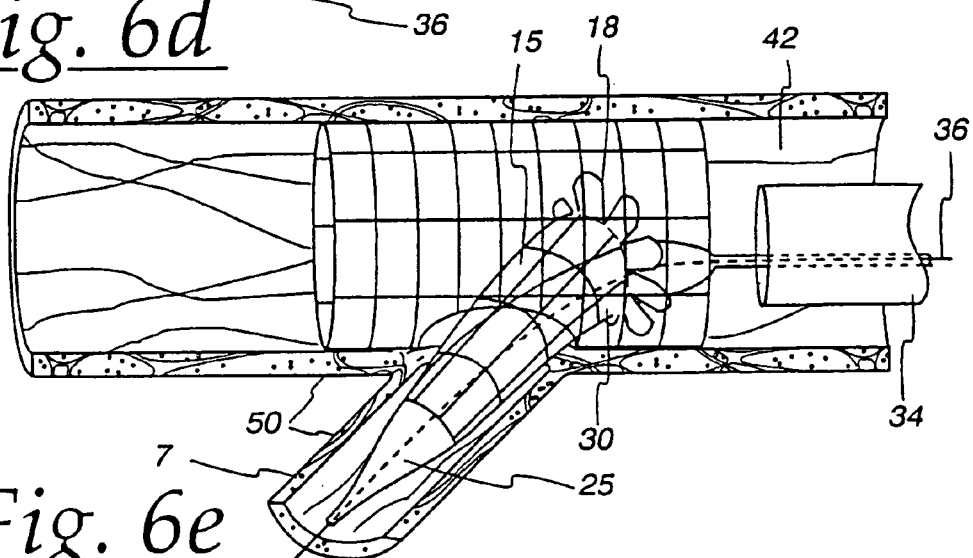
FIG. 6d is a schematic depiction of the removal of the protective sheath of the branch stent allowing for full expansion of the contacting portion prior to final placement and deployment.

As shown in yet another embodiment, the stents of the invention are combined to form a bifurcating double stent as illustrated in FIGS. 5 and 6a–g. After insertion of the main stent as described above but prior to expansion of the main stent (FIG. 6a), the branch stent 15 is inserted through a side opening 16 of the main stent 12, a guidewire 36 and a stabilizing catheter 44 are inserted through the side opening 16 in the main stent 12, and into a branch vessel 7 (FIG. 6a). The stabilizing catheter 44 is used to place the side opening 16 in the main stent 12 over the bifurcation point 50 in the bifurcated vessels 7 and 8 (FIG. 6a). In the embodiment depicted here, the main stent is then deployed into position by inflation of the balloon 24 (FIG. 6b). During insertion and prior to dilation of the branch stent, the branch stent 15 is disposed around the distal end of a branch catheter 54 which may optionally include an inflatable balloon 25, and the contacting portion 18 of the branch stent 15 is held in a collapsed position by a protective sheath 34, as shown in FIG. 6c.

Figure 6E:
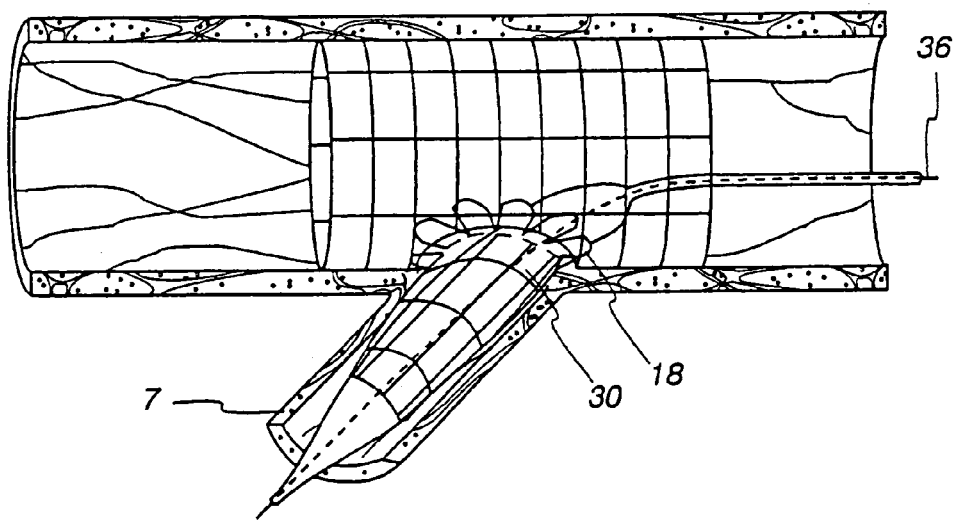
FIG. 6e is a schematic depiction of the compressed branch stent positioned into the branch by the catheter with the contacting portion at least partly contacting the side opening in the main stent, but prior to full expansion of the branch stent.
Figure 6F:
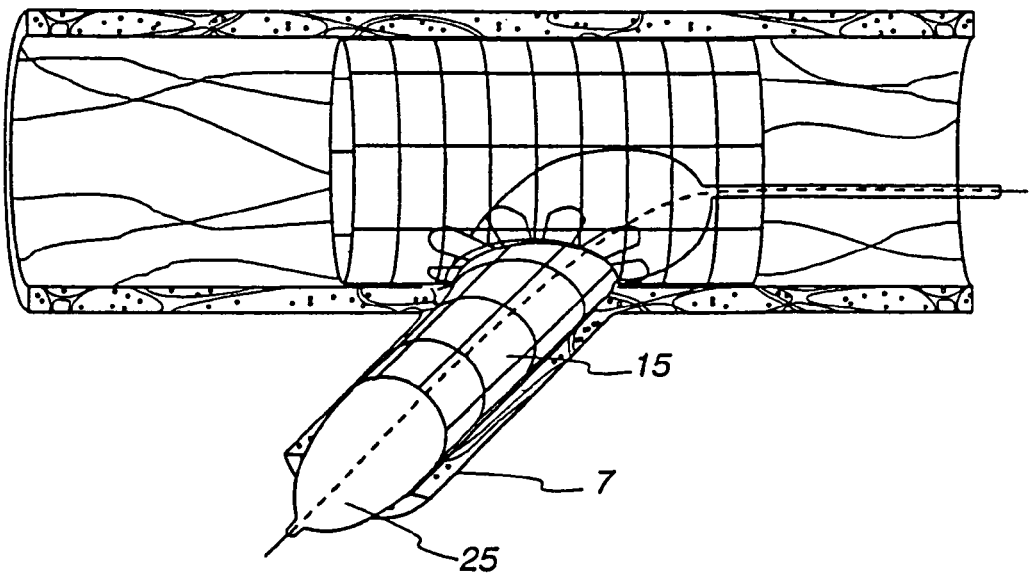
FIG. 6f is a schematic depiction of the fully expanded main stent and the fully positioned and expanded branch stent, where the branch stent is being dilated by inflation of a balloon.
Figure 6G:
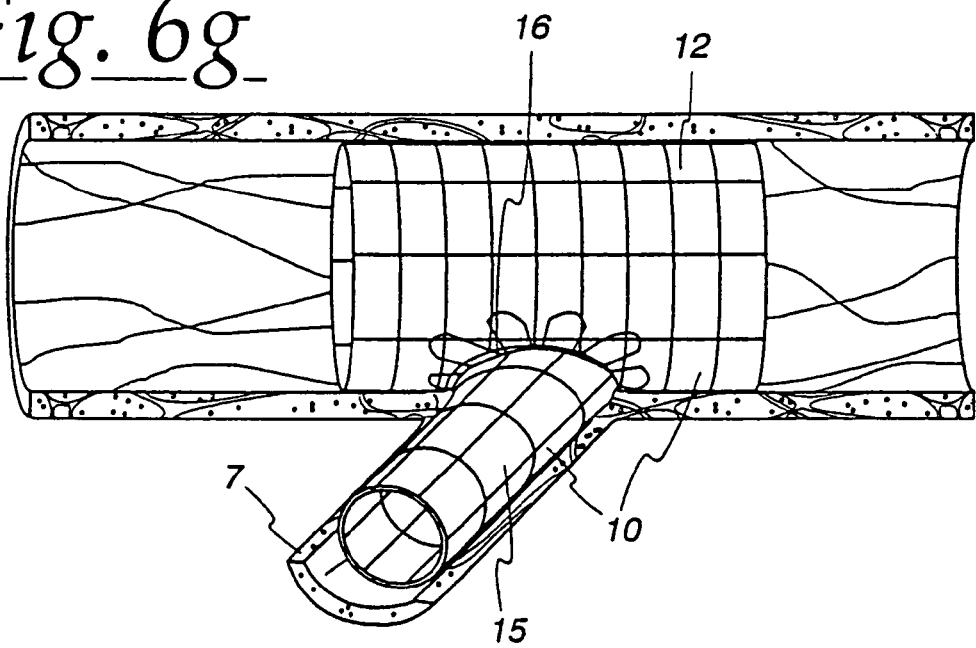
FIG. 6g is a schematic depiction of the fully expanded bifurcating double stent of the invention, positioned into the bifurcation point in a subject vessel.

In the bifurcating double-stent apparatus 10 of the invention, once the main stent 12 is dilated and the stabilizing catheter 44 (as shown in FIG. 6b) is removed, the branch stent 15 is inserted over the branch guidewire 36 and through the opening 16 of the main stent 12 substantially as shown in FIG. 6c, and affixed in place by withdrawal of the protective sheath 34 (FIG. 6d) and insertion of the branch stent 15 until it at least partially contacts the perimeter of the opening 16 of the main stent 12 by the expansion of the contacting portions 18 which are positioned at the proximal end 30 of the expandable stent, as shown in FIG. 6e. The branch stent 15, once positioned in the branch vessel 7, may be then fully expanded by the balloon 25, as shown in FIG. 6f. The angle at which the optionally expandable branch stent 15 is affixed depends upon the vessel structure into which the bifurcating stent apparatus 10 is inserted. All catheters, and guidewires are then withdrawn from the subject vessels, leaving the main stent 12 through which the branch stent 15 is inserted into the branch vessel 7, forming a bifurcated stent 10 (FIG. 6g).

As illustrated in FIGS. 6a–6g, the main stent 12 is deployed prior to the branch stent 15. This is the presently preferred order of deployment. It will be possible, however, in some circumstances to deliver the branch stent 15 prior to the main stent 12. In such cases, the branch stent 15 will be deployed with the contacting portions 18 opened directly against the inner wall of the main blood vessel. The main stent 12 will then be positioned over the contacting portions 18 of the branch stent 15 and firmly expanded thereagainst. A sheath or expansion balloon can be used to properly align the side opening 16 of the main stent 12 with the opening within the contacting portion 18 of the branch stent 15.

Figure 8:
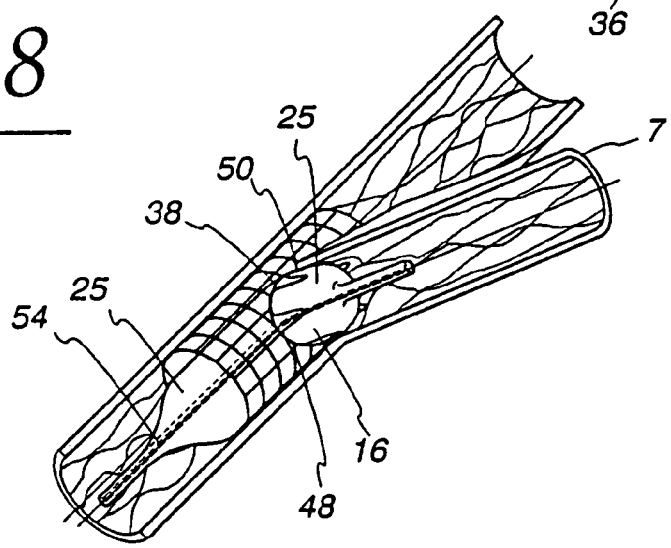
FIG. 8 is a schematic depiction of balloon expansion of the optional expandable portion of the main stent to cover a vessel bifurcation point.
Figure 9:
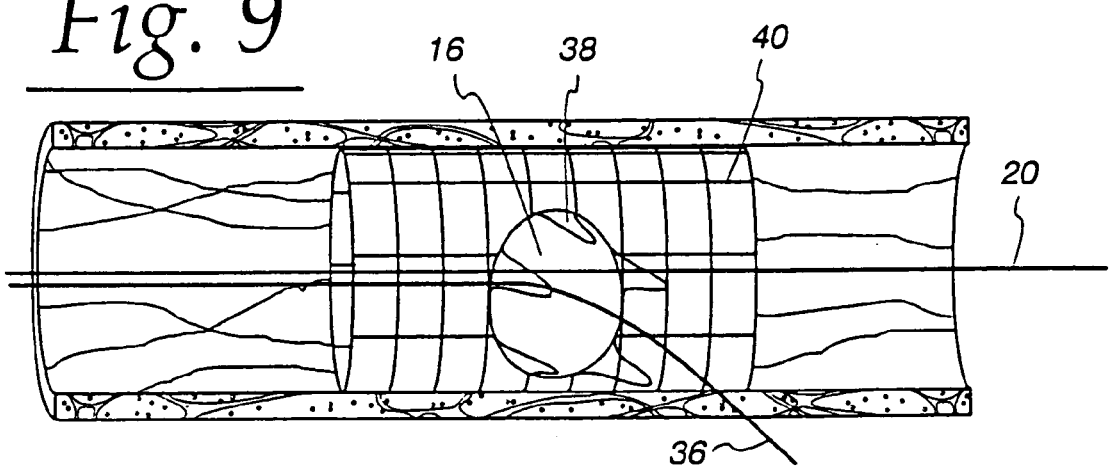
FIG. 9 is a schematic depiction of the main stent with the optional expandable portion fully expanded to extend laterally from the side opening of the main stent.

In the embodiment shown in FIGS. 7–9, the main stent 40 with expandable portion 38 is positioned within the vessel 8 by the guidewires 20 (FIG. 7), and affixed in place by radial expansion of the main stent 40, most particularly by inflation of the balloon 25 (FIG. 8). The main stent is positioned so that the opening 16 is directly over the bifurcation point 50 in the subject vessels 7 and 8 (FIG. 7 and 8). In order to aid such positioning, a side branch guidewire 36 and a stabilizing catheter 44 (as depicted in FIG. 7) are also inserted through the opening 16 of the main stent 40 and through the expandable portion 38 and into the branch vessel 7 (FIG. 8).

The optional expandable portion 38 of the main stent 40 is then expanded radially and in an at least partially perpendicular manner to the sides of the main stent side opening 16 (FIG. 8). In the embodiment illustrated in FIGS. 7 and 8, a balloon 25 is deployed along the side branch guidewire 36 through the expandable portion 38, and inflated until the expandable portion is fully expanded into the branch vessel 7 to cover the bifurcation point 50 of the branched vessel, as illustrated in FIG. 8. In order to extend the expandable portion 38 into the branch vessel 7, a balloon 25 disposed around a branch catheter 54 which is threaded along the side branch guidewire 36, through the main stent 40, through the opening 16 and expandable portion 38, and into the subject branch vessel 7 as shown in FIG. 8. The expandable portion 38 is then extended into the branch vessel 7 by inflation of the balloon 25, which pushes the expandable portion 38 outward radially and lateral to the side opening, into the branch vessel 7 (FIG. 8). Once all catheters and balloons are withdrawn, the expandable portion 38 is arrayed in lateral orientation to the sides of the opening 16 in the main stent 40, and surrounding the opening 16 into the vessel branch (FIG. 9). The guidewires 20 and 36 are then withdrawn from the main and branch vessels.

The expandable portion 38 is illustrated as a plurality of elements which are attached to the peripheral edge of the side opening 16. The elements project radially inwardly into the side opening and thus lie within the cylindrical envelope of the tubular main stent 40 prior to deployment, as shown in FIG. 7. The elements are opened by outward lateral deflection, typically using a balloon catheter, as illustrated in FIG. 8. The deflected elements both traverse the transition between the stent and the lumen of the branch vessel and also serve as an anchor for subsequent placement of the second stent.

In the double stent apparatus of FIG. 5 and in the main stent with expandable portion illustrated in FIGS. 7 and 9, the main stent as well as the expandable portions may be constructed at least partially of and/or coated or plated with an imageable material or marked with imageable markers 56 at suitable locations, including around the perimeter of the side openings of the main stent and at the ends of the expandable portions. In the differentially expandable stent structures of FIGS. 10–12 (described below), a distal portion may be radiopaque with the remainder being radiolucent. Suitable imageable materials are radiopaque, such as gold, tungsten, and the like.

When reinforcing a bifurcated vessel where both branches of the vessel require reinforcing, either 1) the single main stent with the expandable portion is used whereby the expandable portion extends into the vessel branch at least partly covering the origin of the bifurcation, which may be used alone or in combination with any conventional stent; or 2) the main stent without the expandable portion and at least one branch stent with contacting portion are used, the branch stent placed to extend through at least one side opening of the main stent into at least one branch vessel, wherein the branch stent is at least partially in registry and contacting the edge of the side opening through which it extends. The branch stent extends laterally at varying angles to the side opening of the main stent. When treating a bifurcated vessel where the area to he treated spans the bifurcation and unobstructed access to the unstented vessel is required, the main stent may be used either with or without the expandable portion, wherein at least one side opening is placed over the bifurcation point.

The stent apparatus of the invention may be constructed from any non-immunoreactive material, including but not limited to any of the materials disclosed in the prior art stents which are incorporated herein by reference. It is intended that the stent apparatuses of the invention may further be at least partially constructed of, or marked at certain points with, a material which may be imaged, most particularly but not limited to by x-ray and ultrasound.

The stents of the invention may be deployed according to known methods utilizing guidewires and catheters, which are then withdrawn from the subject following deployment of the stents. The subject stents may be self-expanding to conform to the shape of the vessel in which they are deployed, or they may be expanded utilizing balloon catheters, or by any other method currently known or developed in the future which is effective for expanding the stents of the invention. It is contemplated that prior to deployment the stents will be in a collapsed state, and will require either mechanical expansion (such as, for example, by balloon expansion) upon deployment or, for self-expanding stents, will require that the stent be confined to the catheter until deployment by, for instance, a retractable sheath, in which the sheath is removed during deployment and the stent self-dilated. The stents of the invention and the optional expandable portion of the main stent of the invention expand radially from their longitudinal axis, lateral to the side opening of the main stent. Other methods of dilation of the stents of the invention may exist, or may become available in the future, and such methods are contemplated as being within the scope of this invention.

Figure 10:
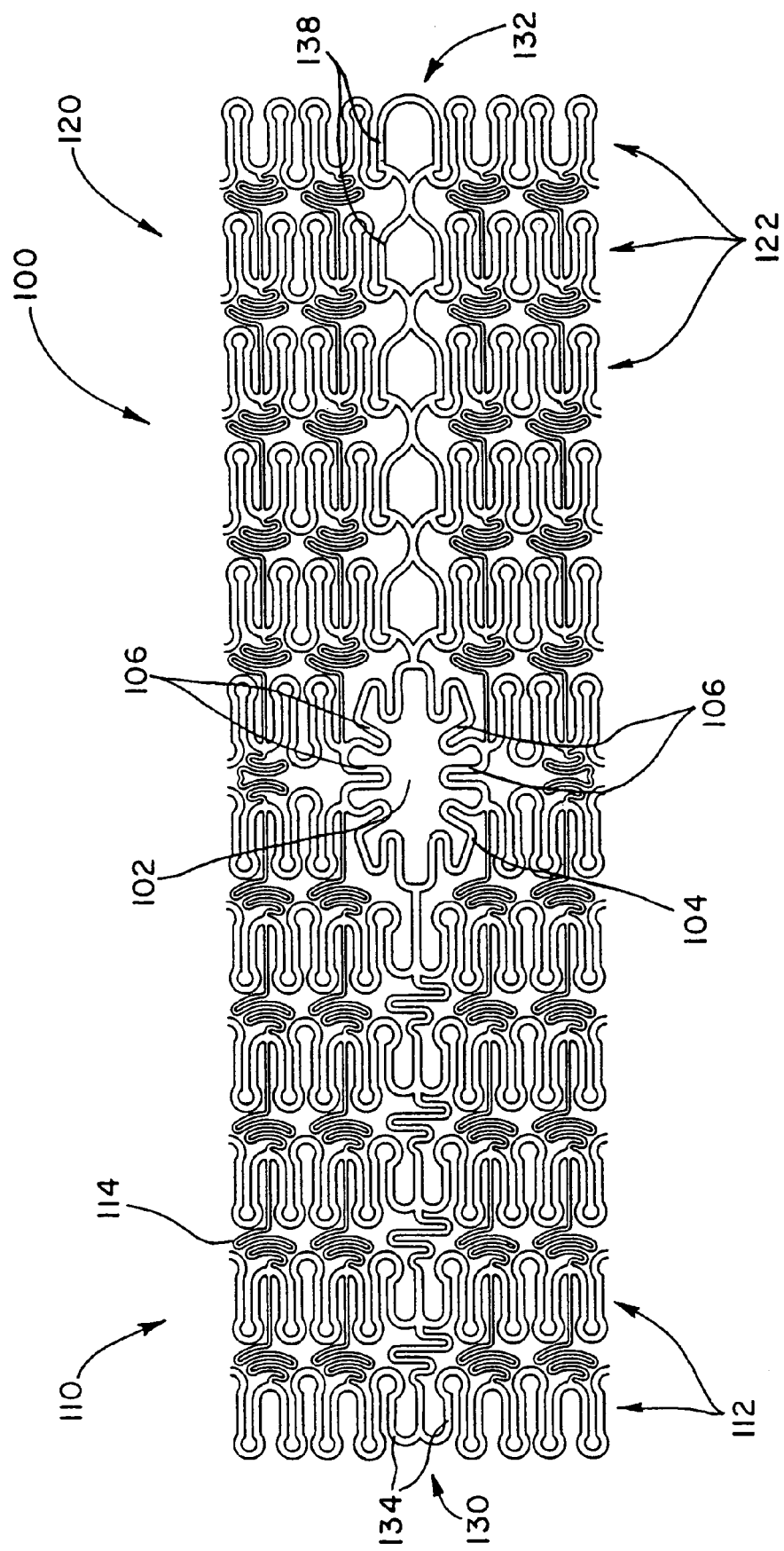
FIG. 10 illustrates a first stent pattern having a side hole and differential expansion characteristics in a "rolled out" view.
Figure 11:
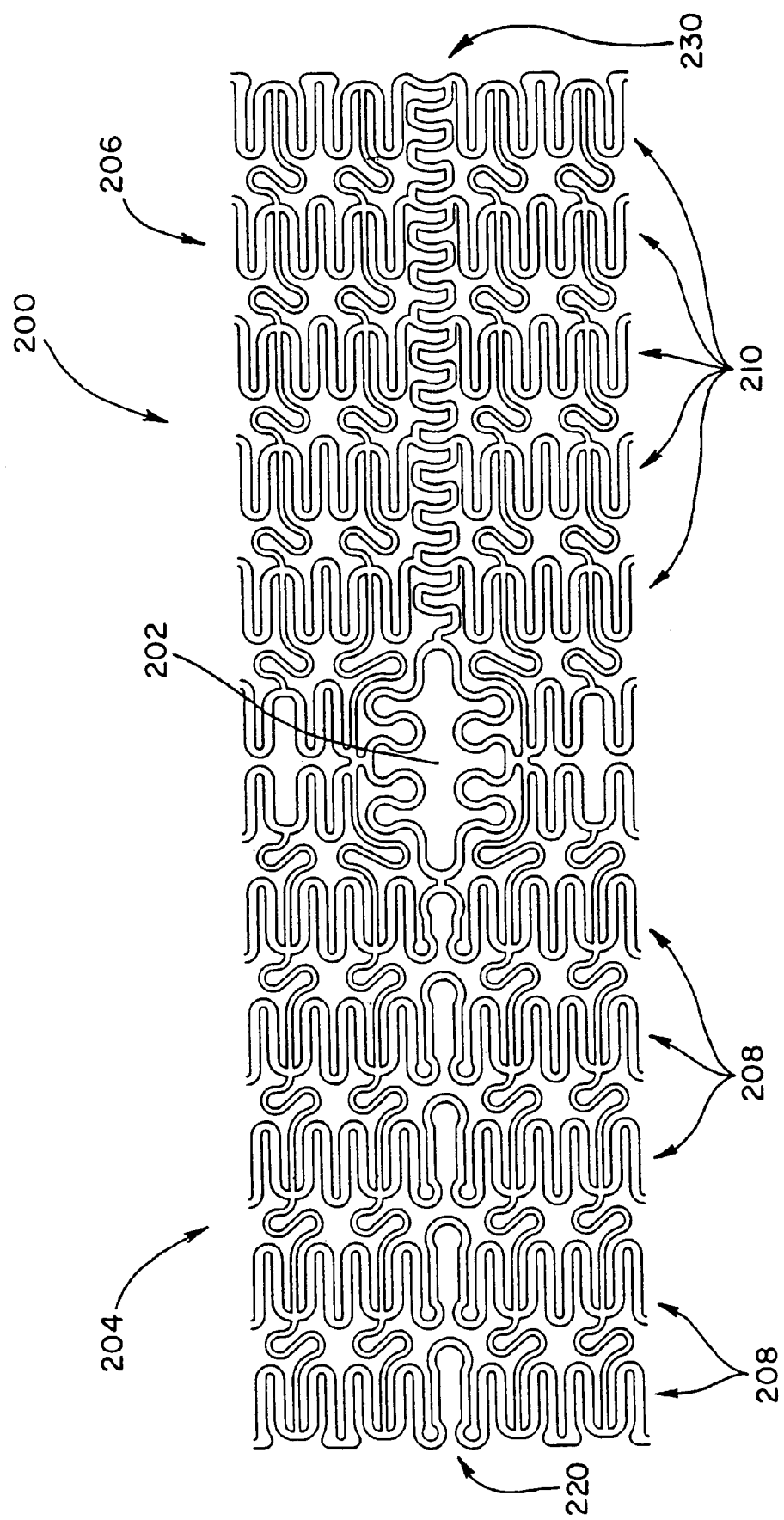
FIG. 11 illustrates a second stent pattern having a side hole and differential expansion characteristics in a "rolled out" view.
Figure 12:
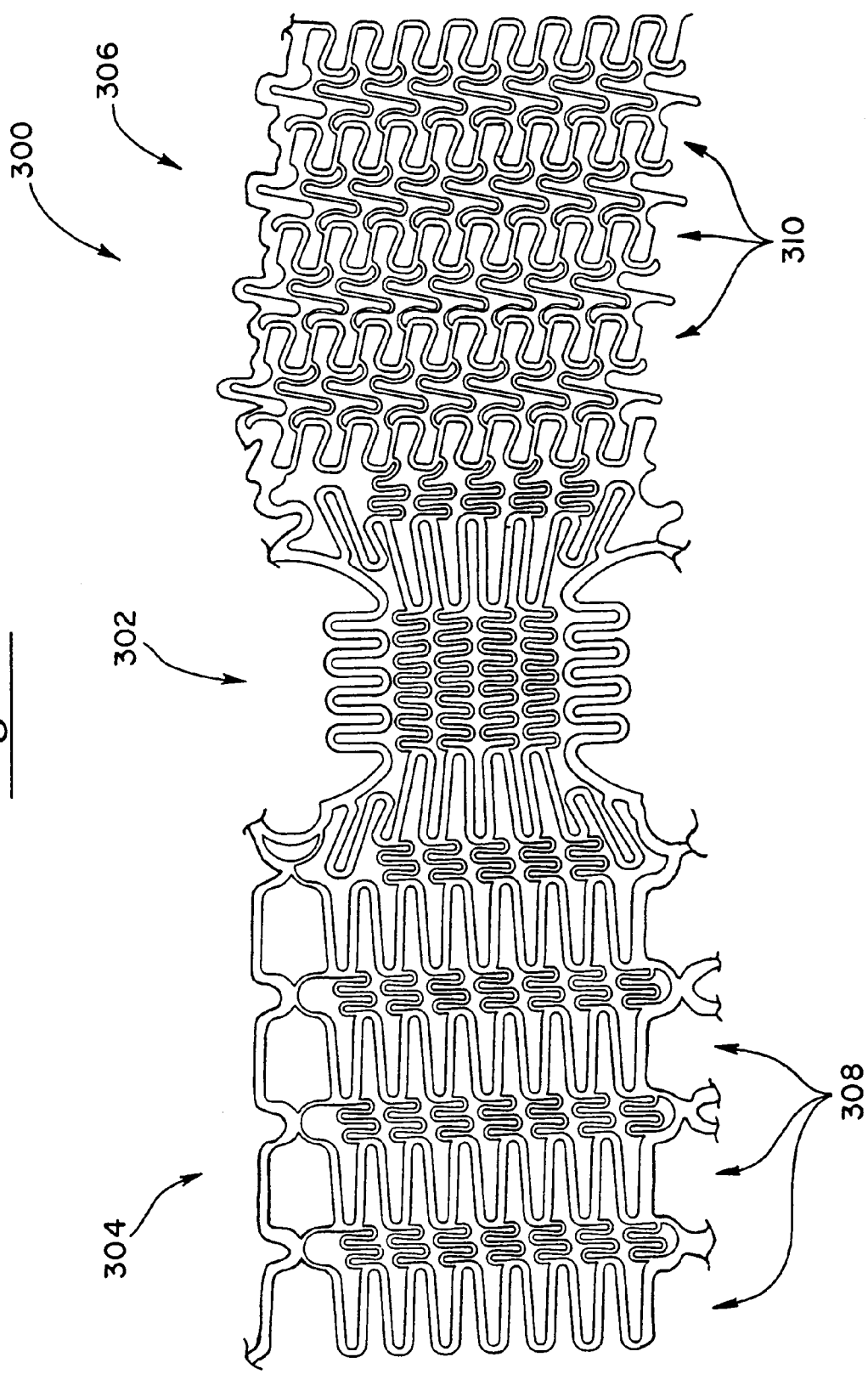
FIG. 12 illustrates a third stent pattern having a side hole and differential expansion characteristics in a "rolled out" view.

Referring now to FIGS. 10–12, the present invention further provides stent structures having differential radial expansion characteristics. In particular, tubular stent structures having side holes, generally as described above, are configured so that a portion of the stent on one side of the side hole will expand at a different yield or threshold force than a portion of the stent on the other side of the side hole. Such different yield forces or pressures may be achieved in a variety of ways. For example, referring to FIG. 10, a stent 100 is illustrated in a "rolled out" view, i.e., the tubular stent is broken along an axial line and then rolled out in the resulting pattern shown in the Figure. The pattern shown in FIG. 10 is prior to expansion. The stent 100 includes a side hole 102 defined by a continuous band 104 having a plurality of loops 106 projecting into the open interior of the side hole. The loops 106 are an integral part of the band 104 and will, prior to expansion or opening, lie within the cylindrical envelope of the tubular body of the stent. The first portion 110 of the stent lies on one side of the side hole 102 and is defined by a plurality of serpentine rings 112. The serpentine rings are joined by axial expansion spring structures 114 so that the stent may be bent as it is introduced and/or deployed. A second portion 120 of the stent 100 is formed on the other side of side hole 102. The second portion is also defined by the plurality of serpentine rings 122 which are generally similar in structure to the rings 112 of the first portion 110. Each of the portions 110 and 120, however, include an axial spine 130 and 132. The axial spine 130 of the first portion 110 comprises simple W-shaped structures including outermost struts 134 which open at a relatively low expansion force on the adjoining hinge regions. In contrast, the axial spine 132 of the second portion 120 comprises box elements 138 which require a greater expansion force to open. Thus, in deployment, the first portion 110 will yield first to allow partial opening before the second portion 120 begins to open.

A second stent structure 200 having differential expansion characteristics is illustrated in FIG. 11. A side hole 202 is formed from a continuous band of material, generally as described for FIG. 10. A first portion 204 and second portion 206 of the stent each comprise a plurality of serpentine ring structures 208 and 210, respectively. While the specific geometries differ, the structures of stents 100 and 200 are generally the same, except for axial spine portions 220 and 230 in the first portion 204 and second portion 206, respectively. The first spine portion 220 comprises a simple U-shaped loop having a pair of struts joined by a simple C-shaped hinge region. The spine 220 will thus open at relatively low expansion forces. In contrast, the axial spine 230 of the second portion 206 comprises a serpentine element which allows for axial expansion but does not permit radial expansion at all. Thus, the first portion 204 will begin opening at much lower expansion forces or pressures than will the second portion 206.

A third concept for providing differential expansion is illustrated in FIG. 12. Stent 300 comprises a side hole 302 (which is shown in halves in the illustration), a first portion 304, and a second portion 306. The first portion 304 and second portion 306 each comprise serpentine rings 308 and 310, respectively. Differential expansion, however, is not achieved by providing a particular axial spine region, but rather by having different characteristics in the serpentine rings 308 and 310. The serpentine rings 308 have axially aligned struts joined by simple hinge regions. The length of the struts is relatively long (compared to those in the second portion 306 as described below) so that the rings will open at a lower expansion pressure or force. The serpentine rings 310 of the second portion 306 have relatively short axial struts defined by hinge regions each having two bands. Such structures require a greater expansion force than do the serpentine rings 308 of the first portion.

Figure 14A:
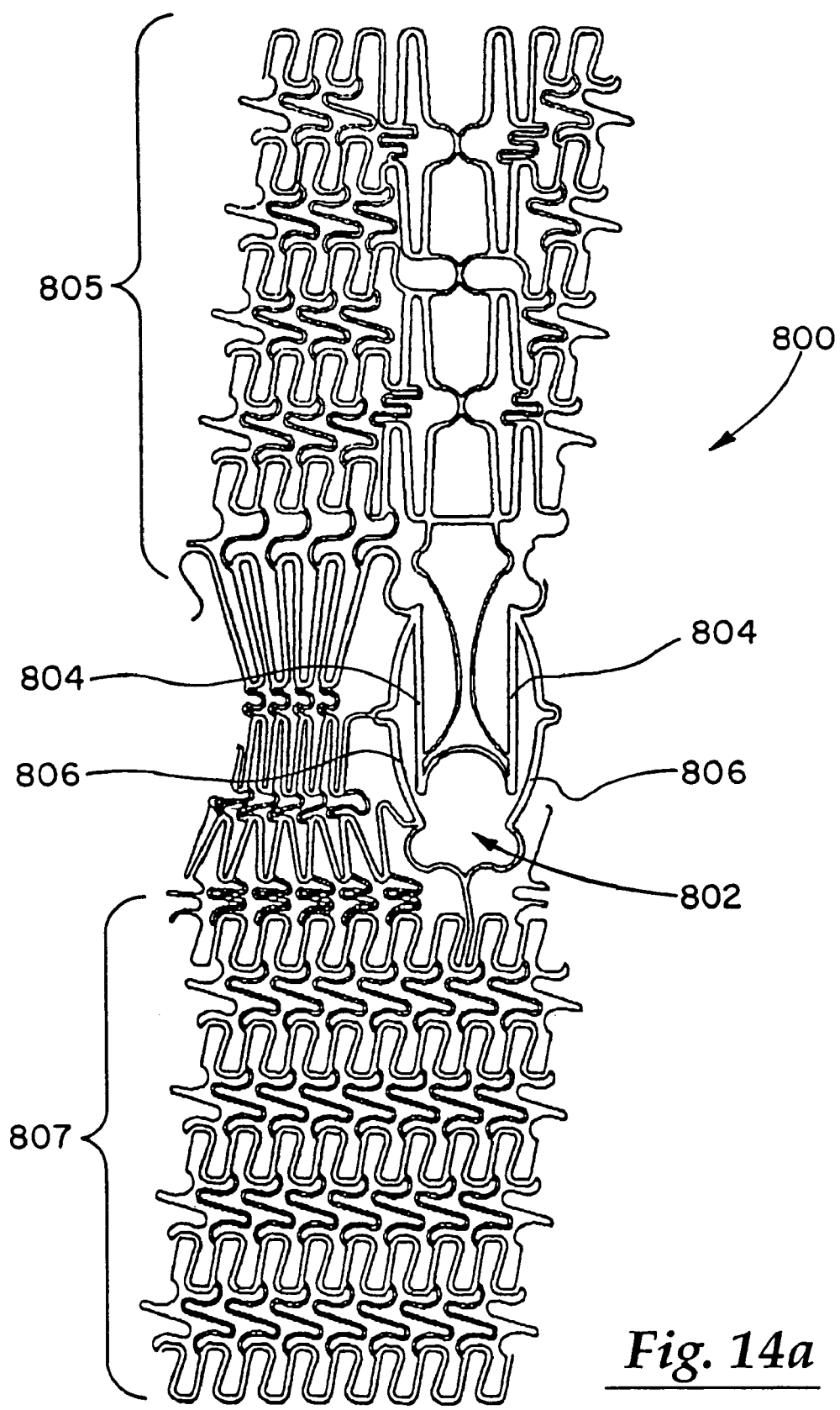
FIG. 14A illustrates a fourth stent pattern having a side hole and differential expansion characteristics in a "rolled out" view.
Figure 14B:
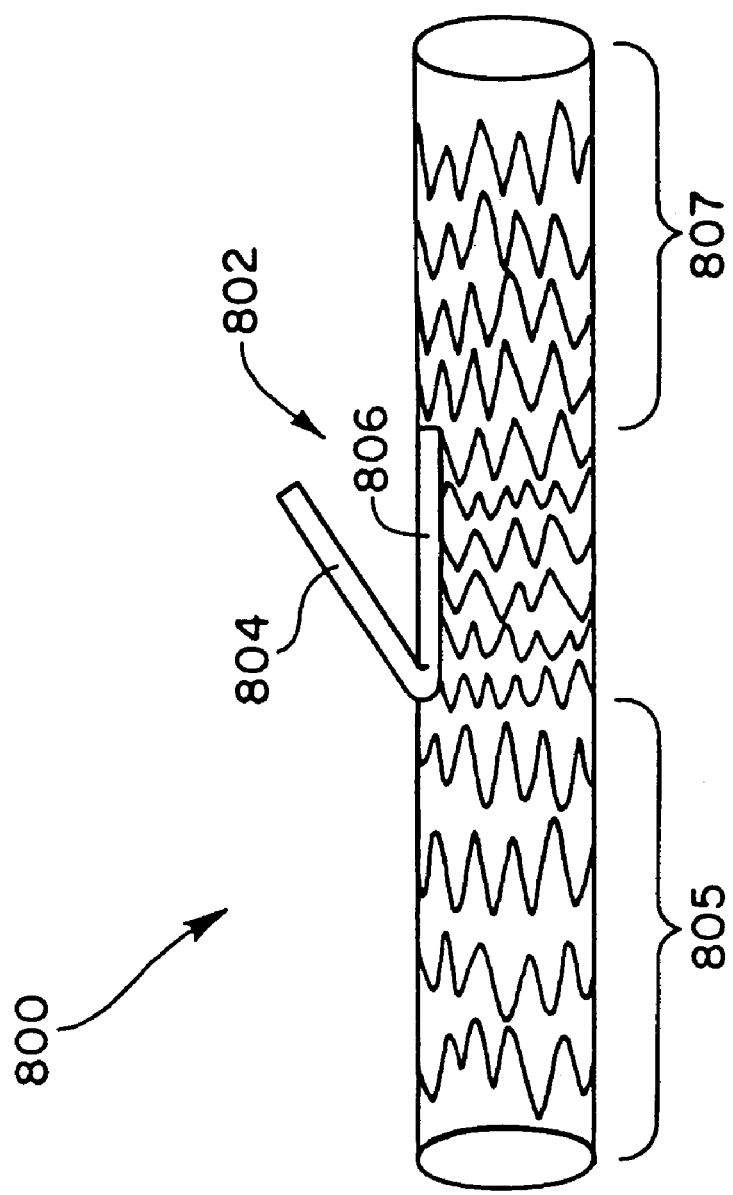
FIG. 14B shows a stent of FIG. 14A with first portion 804 protruding outwardly as a flap during stent expansion.

A fourth concept for providing a differential expansion stent is illustrated in FIGS. 14A and 14B. Stent 800 comprises a side hole 802 which is defined by parallel struts 804 and curved struts 806. Struts 804 can be expanded radially outwardly, forming a flap during stent expansion as illustrated schematically in FIG. 14B. Accordingly, struts 804 can be positioned to support the proximal section of a bifurcated vessel during stent expansion. As described above, portion 805 of stent 800 will preferentially expand at a different rate than portion 807 of stent 800.

Figure 15:
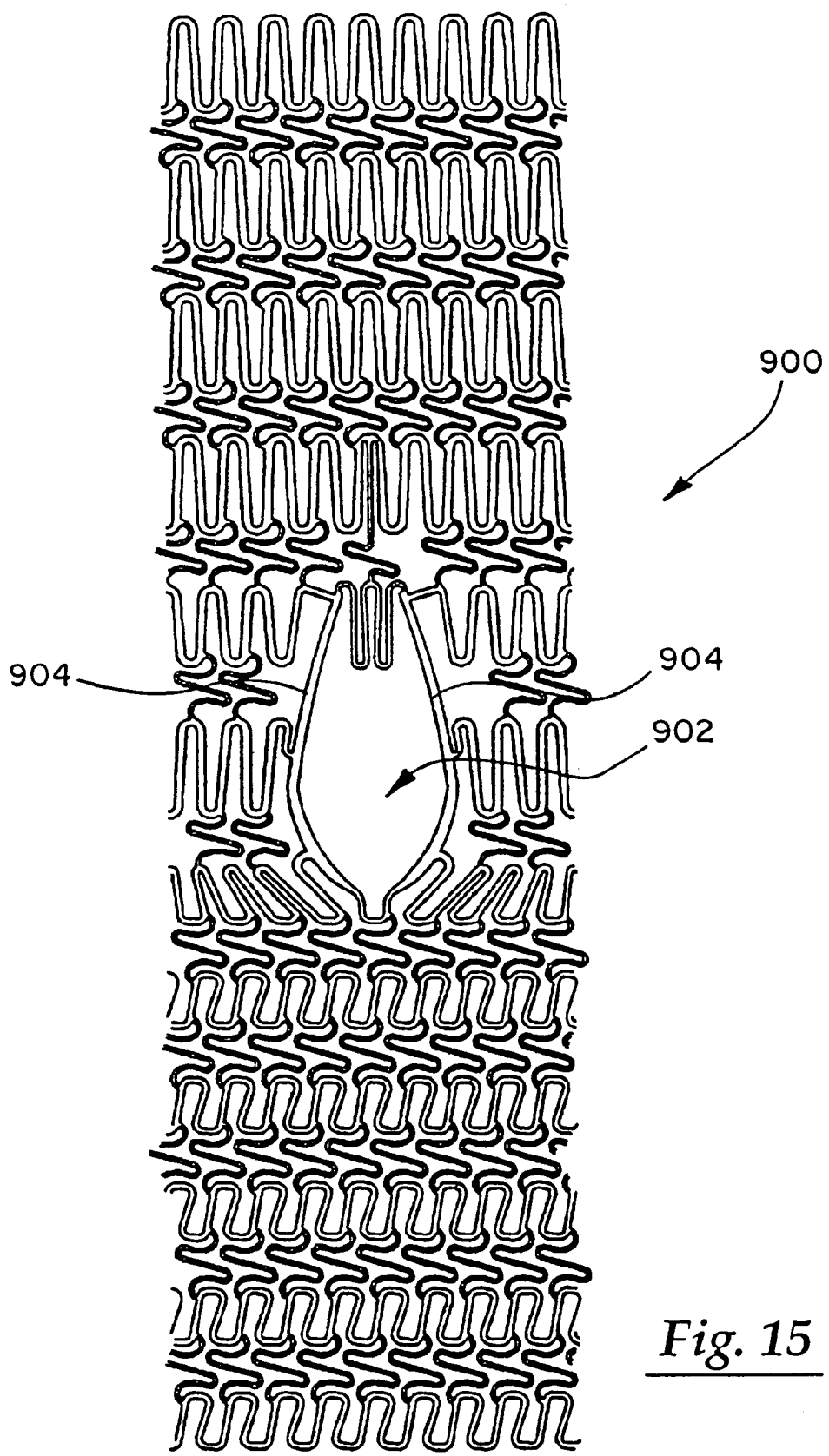
FIG. 15 illustrates a fifth stent pattern having a side hole and differential expansion characteristics in a "rolled out" view.
Figure 16:
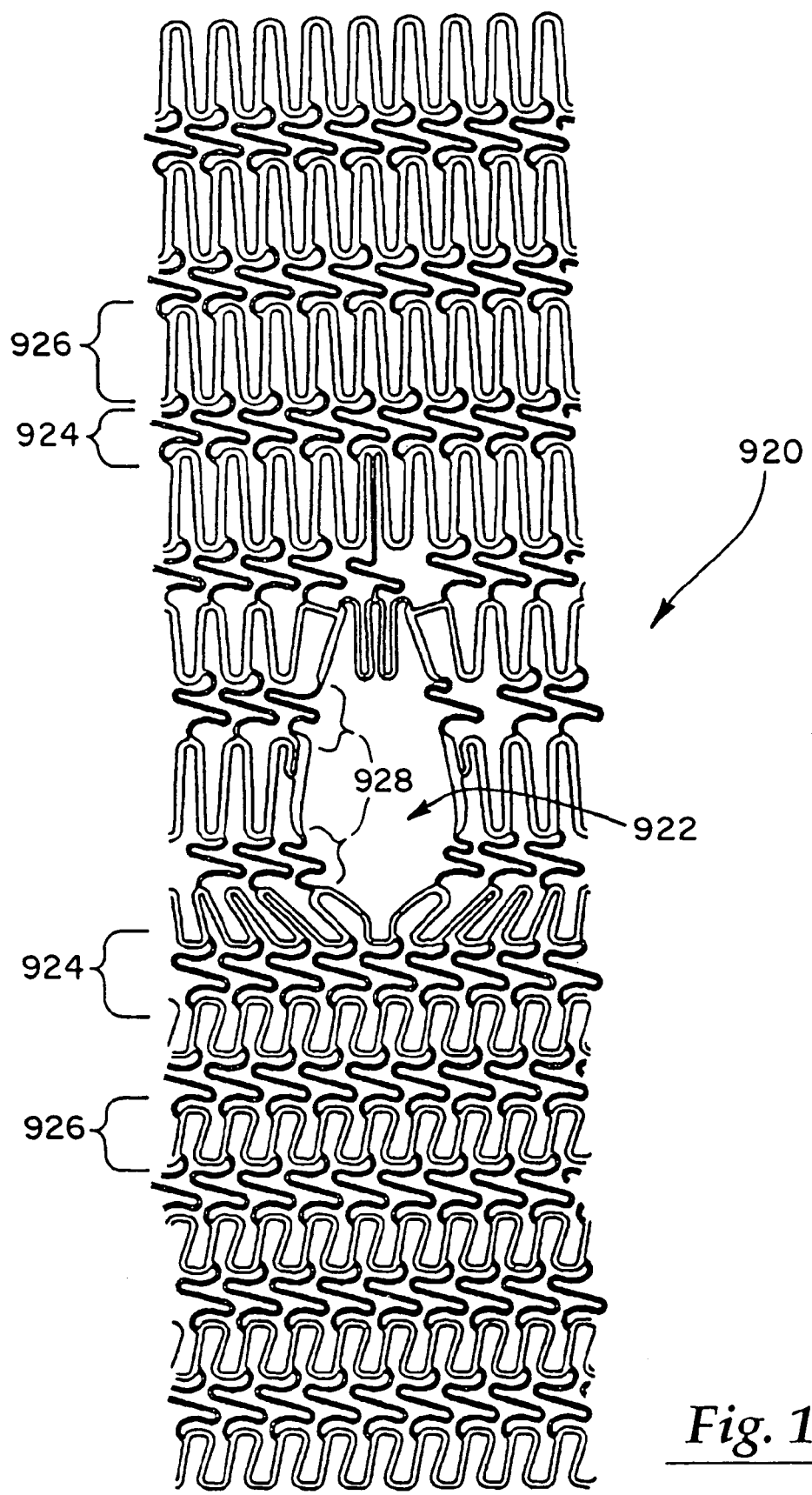
FIG. 16 illustrates a sixth stent pattern having a side hole and differential expansion characteristics in a "rolled out" view.

A fifth differential expansion stent 900 is illustrated in FIG. 15. Stent 900 has a side hole 902 which is tear-drop shaped, offering the advantage of easier expansion of the strut members 904 during differential expansion the stent 900.

A sixth differential expansion stent 920 has side opening 922. Wavy bridges 924 connected to horizontal strut members 926 are adapted to provide superior flexibility in axial bending. Wavy bridges 928 around the perimeter of side opening 922 operate to provide axial flexibility about the side hole 922.

Figure 17:
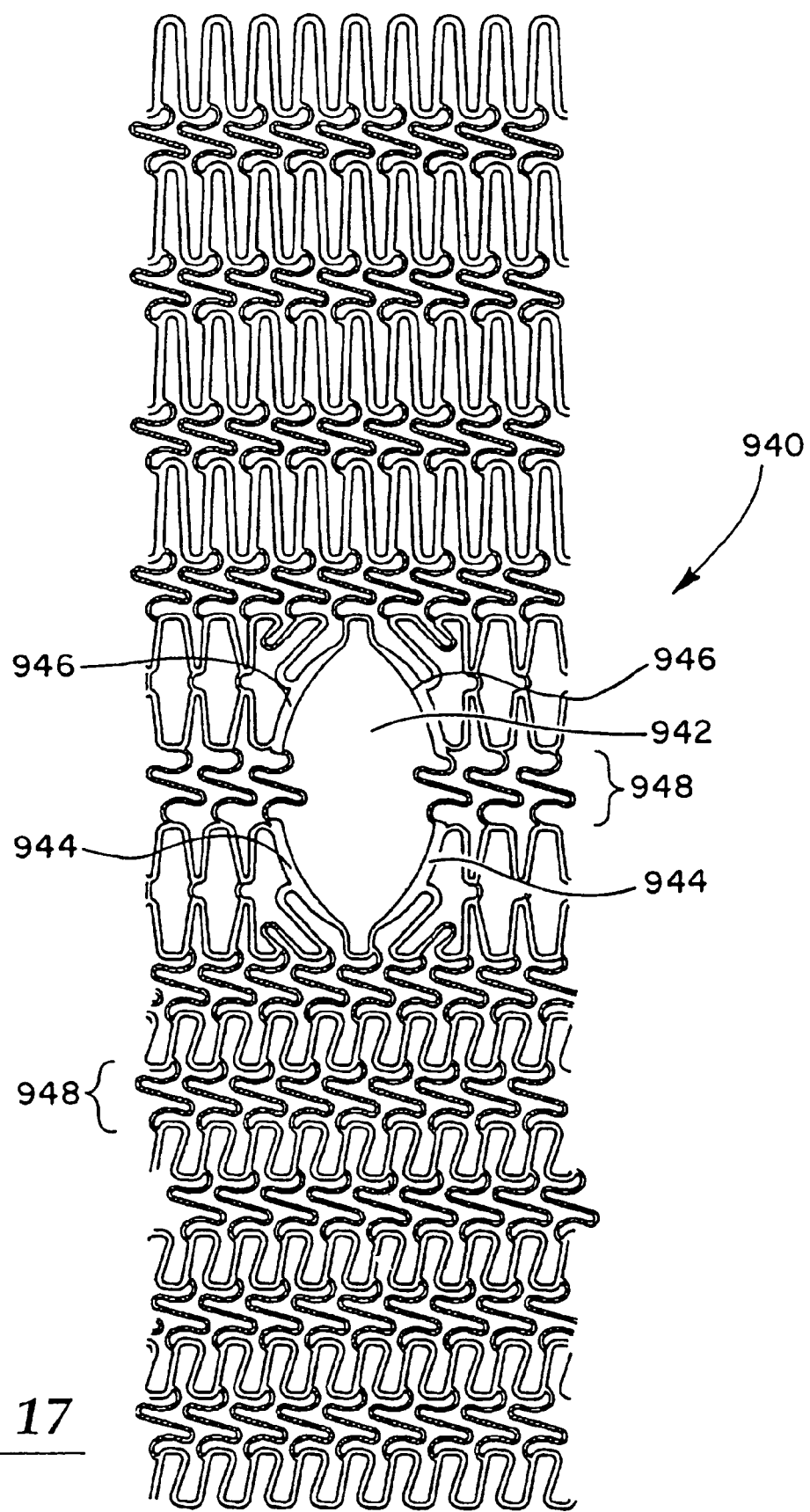
FIG. 17 illustrates a seventh stent pattern having a side hole and differential expansion characteristics in a "rolled out" view.

A seventh differential expansion stent 940 is shown in FIG. 17. Stent 940 has a side hole 942 which is oval in shape and comprised of pair of long struts 944 and 946 at opposite sides of side opening 942 as shown. Wavy bridges 948 facilitate axial bending.

It will be appreciated that numerous other specific designs may be provided for differential expansion. What is important to the present invention, however, is that at least a portion of the stent on one side of the side hole, usually the entire length of the stent on that side of the side hole, will be able to open prior to opening of the stent on the other side of the side hole. Preferably, the first portion of the stent will open at a balloon expansion pressure in the range from 1 atmospheres to 10 atmospheres, while the second portion of the stent will open in response to a balloon expansion pressure in the range from 2 atmospheres to 18 atmospheres.

Referring now to FIGS. 13A–13H, deployment of stent 100 will be described. While reference is made to stent 100, it will appreciated that the same method could be used as well with either of stents 200 or 300. Initially, a pair of guidewires GW1 and GW2 will be deployed in the lumen, typically a bifurcated blood vessel, so that guidewire GW1 extends through the main lumen of the main vessel past the ostium O of the branch vessel BRV. The second guidewire GW2 will be advanced through the lumen of the main vessel and into the lumen of the branch vessel BRV, as illustrated in FIG. 13A. The stent 100 will then be introduced over the guidewires on a delivery catheter 400 having an expansion balloon 402, where the stent is crimped over the expansion balloon. A sheath 404 is disposed in the second portion 120 of the stent with its distal tip (not shown) terminating immediately before the side opening 102. The assembly of the stent 100, delivery catheter 400, and sheath 404 will be delivered with the first guidewire GW1 passing through a guidewire lumen of catheter 400 and the second guidewire GW2 passing through the sheath 404, as illustrated in FIG. 13B. Initial alignment of the side hole 102 of stent 100 is achieved by advancing the stent so that the side hole lies close to the ostium O.

After an initial rough alignment is achieved, the balloon 402 is inflated to an initial inflation pressure which opens the first portion 110 but which leaves the second portion 120 in its substantially unexpanded configuration, as shown in FIG. 13C. Such partial opening allows the sheath 404 to be advanced over guidewire GW2 to better align the side hole with the branch vessel BRV, as shown in FIG. 13D. The sheath provides much greater stiffness than the guidewire, permitting manipulation of the partially deployed stent 100 to achieve the better alignment.

Referring now to FIG. 13E, after alignment is achieved, the balloon 402 will be inflated to a greater inflation pressure to open the second portion 120 of the stent 100 as well. A balloon catheter can then be advanced over the second guidewire GW2 so that balloon 502 can be expanded within the side opening 102 to open the loops 106, as illustrated in FIG. 13F. In many cases, this will be sufficient deployment for the stent where the loops provide the necessary anchoring and transition at the ostium O.

Optionally, a secondary stent 600 may be introduced as illustrated in FIGS. 13G and 13H. The stent 600 is introduced over a balloon 702 on balloon catheter 700. The final deployment configuration is illustrated in FIG. 13H.

It is intended that the invention include all modifications and alterations from the disclosed embodiments that fall within the scope of the claims of the invention.

What is claimed is:

1. A stent for placement in a bifurcated body lumen, the stent comprising:
   a body defining a first substantially cylindrical volume when configured in a first collapsed position and a second substantially cylindrical volume when configured in a second expanded position, the second substantially cylindrical volume being greater than the first substantially cylindrical volume being greater than the first substantially cylindrical volume, the body including:
   a first open end;
   a second open end; and
   a deflectable element having a first position when the body is in the first collapsed position and a second position when the body is in the second expanded position such that when the deflectable element is in the first position the deflectable element defines a first collapsed side access opening and is disposed in the first substantially cylindrical volume, and when the deflectable element is in the second position the deflectable element defines a second expanded side opening different in shape than the collapsed side opening and the deflectable element extends outside of the second substantially cylindrical volume, the deflectable element comprising a plurality of deflectable members, the plurality of deflectable members spaced about the perimeter of the side opening.

2. The stent according to claim 1, wherein the deflectable members extend radially inwardly relative to the side opening when the deflectable members are in the first position.

3. The stent according to claim 2, wherein the deflectable members extend perpendicular to the body when the deflectable members are in the second position.

4. The stent according to claim 3, wherein the deflectable members are adapted to be attached to a second stent at a position adjacent to the side opening.

5. A stent for placement in a bifurcated body lumen, the stent comprising:
   a body defining a first substantially cylindrical volume when configured in a first collapsed position and a second substantially cylindrical volume when configured in a second expanded position, the second substantially cylindrical volume being greater than the first substantially cylindrical volume being greater than the first substantially cylindrical volume, the body including:
   a first open end;
   a second open end;
   a deflectable element having a first position when the body is in the first collapsed position and a second position when the body is in the second expanded position such that when the deflectable element is in the first position the deflectable element defines a first collapsed side access opening and is disposed in the first substantially cylindrical volume, and when the deflectable element is in the second position the deflectable element defines a second expanded side opening different in shape than the collpsed side opening and the deflectibie element extends outside of the second substantially cylindrical volume, the deflectable element comprises a single deflectable member;

wherein the body further comprises an axial spine;

wherein the single deflectable member is aligned with the axial spine when the single deflectable member is in the first position wherein the body further comprises a pair of curved struts defining at least a portion of the side opening; and the single deflectable member further comprises a pair of parallel struts extending parallel to the axial spine when the deflectable member is in the first position.

6. A stent for placement in a bifurcated body lumen, the stent comprising:
a body defining a first volume when configured in a first collapsed position and a second volume when configured in a second expanded position, the second volume being greater than the first volume, the body including:
a first open end;
a second open end; and
a side opening having a perimeter; and
a plurality of deflectable members attached to the body at positions about the perimeter of the side opening,
wherein each of the deflectable members has a first position when the body is in the first collapsed position and a second position when the body is in the second expanded position such that when the deflectable members are in the first position the deflectable members extend radially inwardly relative to the side opening and are disposed in the first volume and when the deflectable members are in the second position, the deflectable members extend substantially perpendicularly from the body and extend outside of the second volume.

7. A stent delivery system for treatment of a bifurcated body lumen, the stent delivery system comprising:
a first catheter;
a second catheter; and
a stent disposed on the first catheter and the second catheter, the stent comprising:
a body defining a first volume when configured in a first collapsed position and a second volume when configured in a second expanded position, the second volume being greater tan the first volume, the body including:
a first open end;
a second open end; and
a side opening adapted to receive the second catheter and having a perimeter; and
a deflectable element extending from the body adjacent the side opening being engageable by the second catheter when the body is in the second expanded position, the deflectable element comprising a plurality of deflectable members, the plurality of deflectable members spaced about the perimeter of the side opening,
wherein the deflectable element has a first position when the body is in the first collapsed position and a second position when the body is in the second expanded position and such that when the deflectable element is in the first position the deflectable element extends at the opening and is disposed in the first volume and when the deflectable element is in the second position, the deflectable element extends away from the opening and extends outside of the second volume after engagement with the second catheter.

8. The stent delivery system according to claim 7, wherein the first catheter comprises a first balloon catheter.

9. The stent delivery system according to claim 8, wherein the second catheter comprises a second balloon catheter.

10. The stent delivery system according to claim 7, wherein the deflectable members extend radially inwardly relative to the side opening when the deflectable members are in the first position.

11. The stent delivery system according to claim 10, wherein the deflectable members extend perpendicular to the body when the deflectable members are in the second position.

12. The stein delivery system according to claim 11, wherein the deflectable members are adapted to anchor a second stent to the stent at a position adjacent to the side opening.

13. The stent delivery system according to claim 7, wherein the second catheter extends through the side opening.

14. A stent delivery system for treatment of a bifurcated body lumen, the stent delivery system comprising:
a first catheter;
a second catheter; and
a stent disposed on the first catheter and the second catheter, the stent comprising:
a body defining a first volume when configured in a first collapsed position and a second volume when configured in a second expanded position, the second volume being greater than the first volume, the body including:
a first open end;
a second open end;
a side opening adapted to receive the second catheter and having a perimeter; and
a deflectable element extending from the body adjacent the side opening being engageable by the second catheter when the body is in the second expanded position, wherein the deflectable element has a first position when the body is in the first collapsed position and a second position when the body is in the second expanded position and such that when the deflectable element is in the first position the deflectable element extends at the opening and is disposed in the first volume and when the deflectable element is in the second position, the deflectable element extends away from the opening and extends outside of the second volume after engagement with the second catheter;
wherein the deflectable element comprises a single deflectable member;
wherein the body further comprises an axial spine and wherein the single deflectable member is aligned with the axial spine when the single deflectable member is in the first position;
wherein the body further comprises a pair of curved struts defining at least a portion of the side opening, and the single deflectable member further comprises a pair of parallel struts extending parallel to the axial spine when the deflectable member is in the first position.

* * * * *